(12) United States Patent
Spartiotis et al.

(10) Patent No.: US 8,306,181 B2
(45) Date of Patent: Nov. 6, 2012

(54) SINGLE SENSOR MULTI-FUNCTIONAL DENTAL EXTRA-ORAL X-RAY IMAGING SYSTEM AND METHOD

(75) Inventors: Konstantinos Spartiotis, Espoo (FI); Tuomas Pantsar, Espoo (FI); Henrik Viking Lohman, Helsinki (FI)

(73) Assignee: Oy AJAT Ltd, Espoo (FI)

( * ) Notice: Subject to any disclaimer, the term of this patent is extended or adjusted under 35 U.S.C. 154(b) by 0 days.

(21) Appl. No.: 12/510,346

(22) Filed: Jul. 28, 2009

(65) Prior Publication Data

US 2010/0034340 A1 Feb. 11, 2010

Related U.S. Application Data

(63) Continuation-in-part of application No. 12/134,578, filed on Jun. 6, 2008, now Pat. No. 7,715,526, which is a continuation-in-part of application No. 12/076,039, filed on Mar. 13, 2008, now Pat. No. 7,715,525.

(51) Int. Cl.
*G01N 23/083* (2006.01)
*G21K 1/12* (2006.01)
(52) U.S. Cl. .................. 378/9; 378/4; 378/193
(58) Field of Classification Search .......... 378/4–20, 378/38, 40, 193, 197
See application file for complete search history.

(56) References Cited

U.S. PATENT DOCUMENTS

| | | | |
|---|---|---|---|
| 4,149,079 A | 4/1979 | Ben-Zeev et al. | |
| 6,118,842 A | 9/2000 | Arai et al. | |
| 6,829,326 B2 | 12/2004 | Woods et al. | |
| 7,197,109 B2 | 3/2007 | Rotondo et al. | |
| 7,236,563 B2 | 6/2007 | Sa et al. | |
| 7,315,608 B2 | 1/2008 | Sa et al. | |
| 7,330,763 B1 | 2/2008 | Cullen et al. | |
| 7,336,763 B2 * | 2/2008 | Spartiotis et al. | 378/40 |
| 7,424,091 B2 | 9/2008 | Park et al. | |
| 7,676,022 B2 * | 3/2010 | Pantsar et al. | 378/39 |
| 2001/0048732 A1 | 12/2001 | Wilson et al. | |
| 2004/0000630 A1 * | 1/2004 | Spartiotis et al. | 250/208.1 |

(Continued)

FOREIGN PATENT DOCUMENTS

JP 2006-280844 10/2006

(Continued)

OTHER PUBLICATIONS

J. Hsieh, ed., "Computed Tomography, Iterative Reconstruction", Computed Tomography: Principles, Design, Artifacts and Recent Advances, Jan. 1, 2003, pp. 90-97, XP-002492681.

(Continued)

*Primary Examiner* — Anastasia Midkiff
(74) *Attorney, Agent, or Firm* — Young & Thompson

(57) ABSTRACT

A multi-functional dental extra-oral x-ray imaging system includes a conventional x-ray source and manipulator to control the movement of the x-ray source by translating and rotating, a real time multiple frame producing x-ray imaging device and at least two different exposure profile programs, whereas one of such profiles produces a standard panoramic image and a second of such profiles produces an angled or transverse slice to a the panoramic image. A third exposure profile program produces a substantially linear projection of the human skull by combining two linear projections, one for the right and one for the left part of the head. The sensor is a linear direct conversion operating preferably in the frame mode and producing more than 100 fps.

21 Claims, 28 Drawing Sheets

U.S. PATENT DOCUMENTS

2007/0297564 A1  12/2007  Rotondo et al.
2009/0022270 A1  1/2009   Yoshimura et al.
2009/0041191 A1  2/2009   Suzuki et al.

FOREIGN PATENT DOCUMENTS

| WO | 93/00046    | 1/1993  |
| WO | 00/00085    | 1/2000  |
| WO | 00/00085 A1 | 1/2000  |
| WO | 2004/014232 | 2/2004  |
| WO | 2006/109806 | 10/2006 |

OTHER PUBLICATIONS

IPRP dated Sep. 14, 2010 from PCT/IB2009/000056.
International Preliminary Report on Patentability and Written Opinion, dated Jan. 31, 2012, from corresponding PCT application.

* cited by examiner

SINGLE SENSOR MULTI-FUNCTIONAL DENTAL EXTRA-ORAL X-RAY IMAGING SYSTEM AND METHOD

CROSS REFERENCE TO RELATED APPLICATIONS

This application is a continuation-in-part of U.S. patent application Ser. No. 12/134,578 filed Jun. 6, 2008 and issued as U.S. Pat. No. 7,715,526, which is a continuation-in-part of prior U.S. patent application Ser. No. 12/076,039 filed Mar. 13, 2008 and issued as U.S. Pat. No. 7,715,525. The entire contents of each of these applications are hereby expressly incorporated by reference.

BACKGROUND OF THE INVENTION

The present invention relates to the field of dental extra-oral imaging systems. More specifically the present invention relates to panoramic dental x-ray imaging systems and Computerized Tomography ("CT") dental x-ray imaging systems.

DESCRIPTION OF THE RELATED ART

Digital extraoral dental x-ray imaging systems can be divided into two main categories. The first category is planar imaging systems that produce a flat, two dimensional image. This category includes panoramic, transversal and cephalometric imaging. The second category consists of the so called volumetric imaging systems that produce three dimensional images. These are normally called computed tomography or Computerized Tomography (CT) systems.

The actual systems can have one or more modalities so a single system can provide both modalities utilizing a panoramic imaging device and a volumetric imaging device.

The image of a planar imaging system has two types of resolution: The image spatial resolution along the two axes of the imaging device ("width" and "height" correspondingly) and the resolution in the depth direction (i.e., perpendicular to the imaging layer of the imaging device.)

The spatial resolution depends on the size of the pixel of the imaging device, the inherent modulation transfer function of the imaging device (i.e., the blur function), the accuracy of the mechanical movement and x-ray source characteristics. Usually it is possible to see objects of the size of the pixel of the imaging device, i.e., an imaging device with 100 micron pixel size can resolve objects of 100 microns wide.

Planar X-ray imaging systems produce an image which has the whole content of the object to be imaged projected to a single planar image. This means that all features of the object inside the field of view are seen on the image regardless of the actual distance from the sensor. In most cases it is necessary to eliminate the effect of features or objects outside a selected region of interest. For example, in a panoramic image, the shadow of the spine should be eliminated. The depth resolution means how small is the area that will have perfectly focused projection in the image. Other regions outside this area appear blurred or disappear completely. The depth resolution mainly depends on the width of the sensor along the direction of movement, the actual movement trajectory and spatial resolution of the imaging device. The difference between spatial and depth resolution depends almost solely on the angular range from which any point in object to be imaged in seen. The larger the angular range, the better the depth resolution, i.e., smaller objects can be resolved depth wise. With the above in mind the extra oral system performing panoramic imaging the sensor is typically long and with a small width but does not produce any frames and is not capable of doing transverse slices. The dual purpose extra-oral systems have a second sensor that is a flat panel of some kind with m/n equal or very close to 1, and where m is the length and n the width of the flat panel. The length and width of flat panels is usually in the range of 5 cm to 20 cm in most dental extra-oral imaging systems.

Conventional panoramic x-ray imaging systems ("pan"), digitized with some kind of, usually, CCD sensor, have existed for the past 15 years. Such conventional or standard dental panoramic x-ray imaging systems, can be also adapted to include a cephalometric ("ceph") arm that will produce a linear projection of the entire human skull. Mostly orthodontists use the panoramic systems with or without the ceph arm, which is useful but typically will add significantly to the cost for the dentist.

Advanced pan systems, have included a second sensor, which is typically a small flat panel. Such is usually a CCD type of flat panel with dimensions of 10 $cm^2$ up to 30 $cm^2$ (typically). For example, such a system is described in US2006/0233301 A1, with two sensors side by side. The first sensor is a panoramic sensor and the second one is a flat panel. When the flat panel is used with a CT movement profile which involved mostly rotation by at least 180 degrees, a volumetric 3D image is produced. The second sensor can also be used to produce transverse slice images, i.e., images that are approximately at right angles with respect to the panoramic layer with substantially linear movement. Several such systems, with dual sensor, are available in the market today. The addition of a second sensor makes the system much more expensive for the doctors. Furthermore the ceph arm is still needed for a doctor who wants to have a ceph image. Therefore a complete system would require a first sensor to make a panoramic image, a second sensor/flat panel to make transverse slices and/or 3D images and a ceph arm, where the panoramic sensor would be attached as a snap-on in these cases where a ceph image is needed.

Beyond the advanced pan systems, there exist the very expensive dental CT systems, with large area flat panels. The flat panel are square and have active areas more than 100 $cm^2$. Such systems cost for the doctor typically in the range of 100 kUSD-200 kUSD. Therefore the price is forbidding to most private practitioners. Such systems are used currently by implantologists and large clinics. Furthermore the dental CT systems have the capability to produce all of the needed panoramic images and transverse slices and 3D volumes, but the quality of the basic or standard panoramic image is much worse than the quality of a panoramic image produced with a five times cheaper standard digital pan system. So the doctor who wants to have transverse slices, 3D images but also excellent quality pan images would still have to buy the hugely expensive dental CT system and still a pan system. The reason why the dental CT systems do not make good quality pan images is that the flat panels used are large in area with low frame rate speed which does not exceed 30 fps. At that low speed, the CT system is not able to do a standard pan exposure and the images come out blurred.

Therefore there is a problem to be solved, namely a dental extra-oral x-ray imaging system that can provide at least two different functions, with a simpler and less expensive structure.

One solution was proposed in U.S. application Ser. No. 11/277,530 assigned to the assignee of the current invention. In accordance with Ser. No. 11/277,530 a dental extra x-ray imaging system is provided where with a single panoramic profile exposure the system provides a standard panoramic image, several non-standard panoramic layers, transverse slices and even 3D images of limited volumes. Such a system obviously is unique in that it provides most of the needed dental images with a single sensor and a single exposure profile, namely the panoramic profile. However the inventors of the current invention have realized that in practice the panoramic profile is specifically designed so that the x-ray source and imaging device move along a path in a way that produces optimal panoramic images, but sub-optimal or very blurry or even unusable transverse slices (to the panoramic layer) and even worse 3D images. Furthermore Ser. No. 11/277,530 stays silent on the issue of providing a ceph type of image, namely a linear projection of the human skull or part of the human skull.

SUMMARY OF THE INVENTION

In accordance with one aspect of the current invention, there is a an extra-oral dental x-ray imaging system comprising an x-ray source exposing x-rays to an object to be imaged; a single x-ray imaging device suitable for producing multiple frames during at least part of the exposure, the single x-ray imaging device has an active area with a long dimension m and a short dimension n with $m/n \geq 1.5$ (one point five); manipulator for moving along a path the imaging device between consecutive radiated frames during exposure, the manipulator enabling movement of the x-ray source and the imaging device by means of selective translation and selective rotation about at least one rotational axis located between a focal point of the x-ray source and the x-ray imaging device; said extra-oral dental x-ray imaging system having at least one exposure profile program for producing a local 3D volumetric image or a slice at an angle to a panoramic layer image for a sub-volume of interest, said profile characterized in that during the exposure a majority of the points, in said sub-volume of interest, are projected in said x-ray imaging device with an angular range $\beta$, satisfying the relationship $\beta/\alpha > 2.1$, where $\alpha$ is the angle of the x-ray imaging device as seen from the x-ray focal spot, i.e., the aperture angle of the sensor.

In the context of the invention, an exposure profile is a path or trajectory along which the assembly of the x-ray source and the imaging are moving in order to expose to radiation part or all of the human head, including the jaws and teeth. An exposure profile need not to have x-ray emitted continuously in that the human head may be exposed only during part of the profile. The x-ray tube may be of an AC or DC type and x-rays may even be emitted in a pulsed manner. The x-ray source and the imaging device may be attached in a fixed geometry to one another or in rare cases the geometry may vary with movable mechanical parts.

In accordance with a second aspect of the current invention, there is an extra-oral dental x-ray imaging system comprising an x-ray source exposing x-rays to an object to be imaged; an x-ray imaging device suitable for producing multiple frames during at least part of the exposure, the x-ray imaging device has an active area with a long dimension m and a short dimension n with $m/n \geq 1.5$ (one point five), manipulator for moving along a path the imaging device between consecutive radiated frames during exposure, the manipulator enabling movement of the x-ray source and the imaging device by means of selective translation and selective rotation about at least one rotational axis located between a focal point of the x-ray source and the x-ray imaging device; said extra-oral dental x-ray imaging system having an exposure profile program for producing a substantially linear projection of at least part of said object to be imaged said profile comprising at least two substantially linear sections. The linear projection is preferably a cephalometric image of the human skull.

In a third aspect of the current invention, in order to achieve a panoramic projection image as well as a cephalometric projection image with a single sensor and without the use of a ceph arm, the distance of focal spot of the x-ray source to the image device is less than 1.5 m (one and a half meters) and preferably less than 0.7 m (seventy centimeters), and the distance of the imaging device to the nearest face of the object/skull to be imaged is no more than 20 cm and preferably no more than 10 cm.

The current invention discloses a dental extra-oral x-ray imaging system that is multi-functional producing at least a panoramic layer image, but also has exposure profiles that produce transverse slices, namely images corresponding to a slice that is at an angle with respect to a volume of interest of the panoramic layer image. The current invention also describes a system that can in addition or alternatively produce a linear cephalometric projection of the human skull or part of the human skull, but without using the traditional ceph arm.

The x-ray source and the imaging device are mounted preferably both on a mechanical pi shaped structures, which under the control of a manipulator will translate selectively and rotate selectively. This can be accomplished by means for example of two or more motors, one motor moving in the x direction and the other motor rotating. More preferably the system has three motors, two of the motors providing translation in the x,y direction and the third motor rotating.

The combination of motors and a control unit (usually a CPU or EPROM) is referred to as the manipulator as it manipulates the movement of the x-ray source and/or the imaging device. The manipulator can be pre-programmed to execute several exposure profiles, meaning that different programs correspond to different exposure profiles, and an exposure profile is a path along which the x-ray source and/or imaging device move during an exposure.

The imaging device is of the type that is linear, with a long dimension m and a sort dimension n, such that $m/n \geq 1.5$, and more preferable $m/n > 3$ and even more preferably $m/n > 6$. The choice of the imaging device to be rectangular with elongated linear shape is very important because such imaging device (sensor) is able to operate at high frame rates of more than 50 frames per second ("fps"), more preferably more than 100 fps and even more preferably in the range of 150 fps to 500 fps. With an elongated, fast imaging device the current invention produces very high quality panoramic images (because of the high speed), while maintaining a low cost. Preferably the imaging device is a CdTe-CMOS (Cadmium Telluride-CMOS) or CdZnTe-CMOS (Cadmium Zinc Telluride). Such imaging device combines excellent detection efficiency and excellent resolution with high speed.

A conventional dental transversal imaging system of the prior art uses an expensive wide imaging sensor and a mostly linear movement profile with no or very little rotation. The system in accordance with the current invention uses the linear and inexpensive, fast with real time frame output imaging device, as described above, and moves during the exposure the x-ray source and imaging device along a path that is a combination of selective translations and selective rotations such that substantially every point in the sub-volume of interest is projected in the x-ray imaging device from different angles in an angular range $\beta/\alpha > 2.1$, where $\alpha$ is the angle of the x-ray imaging device as seen from the x-ray focal spot. In such a way the frames produced by the imaging device are utilized by a processor running an algorithm that reconstructs an image of a slice that is at angle with respect to the panoramic layer.

Alternatively or in addition, the linear imaging device and x-ray source can move, in another exposure profile, along a near linear path projecting onto the imaging device one half of the human skull, then by partial translation and partial rotation re-position with respect to the other half of the human skull and then continue the exposure to produce a second substantially linear projection of the second half of the human skull. Then the frames produced by the imaging device during the two substantially linear exposures are combined in a processor utilizing an algorithm to produce a complete substantially linear projection of the human skull, equivalent or equal to a traditional cephalometric image.

The advantages of the current invention are many:
Firstly a single system with a single linear and inexpensive sensor are used to produce several or different functionality images required by the dental practitioner.
The panoramic images as well as the transverse (to the panoramic) images and skull linear projections are all of excellent quality, without compromising one or the other.
The system is much more compact than conventional high end panoramic systems with a ceph arm or dental CT systems.

While the preferred imaging device in the preferred embodiments of the current invention is a CdTe bump-bonded to CMOS or CdZnTe bump bonded to CMOS direct conversion, other frame producing imaging devices with m/n≧1.5 can be used without departing from the scope of the invention. For example nanno phosphor indirect conversion detector can be coupled to CMOS or CCD and be used as an imaging device, or regular phosphors or scintilators can also be used. Alternatively epitaxially grown CdTe and CdZnTe applied on a CMOS, CCD or flat panel can be used. Alternatively a frame producing CCD or other type of CMOS sensors or flat panel can be used.

Yet in another preferred embodiment of the current invention we provide an extra-oral dental x-ray imaging system, for performing a partial CT or partial 3D image of a region of interest of an object:

a) an x-ray source for exposing an object to x-rays so that the object may be imaged during the exposure;

b) a single x-ray imaging device suitable for producing multiple radiated image frames during at least part of the exposure,;

c) a manipulator for moving the imaging device and the x-ray source along a path between plural positions corresponding to plural radiated image frames during the exposure, the manipulator enabling movement of both the x-ray source and the imaging device by selective translation and selective rotation about at least one rotational axis located between a focal point of the x-ray source and the x-ray imaging device; and d) an exposure profile program for producing a partial CT or 3D image for said region of interest, said profile characterized in that the axis of rotation is movable along a trajectory during at least part of the exposure.

DETAILED DESCRIPTION OF THE PREFERRED EMBODIMENTS

Prior to discussing the preferred embodiments of the current invention, the prior art will be reviewed.

Figure 1A:
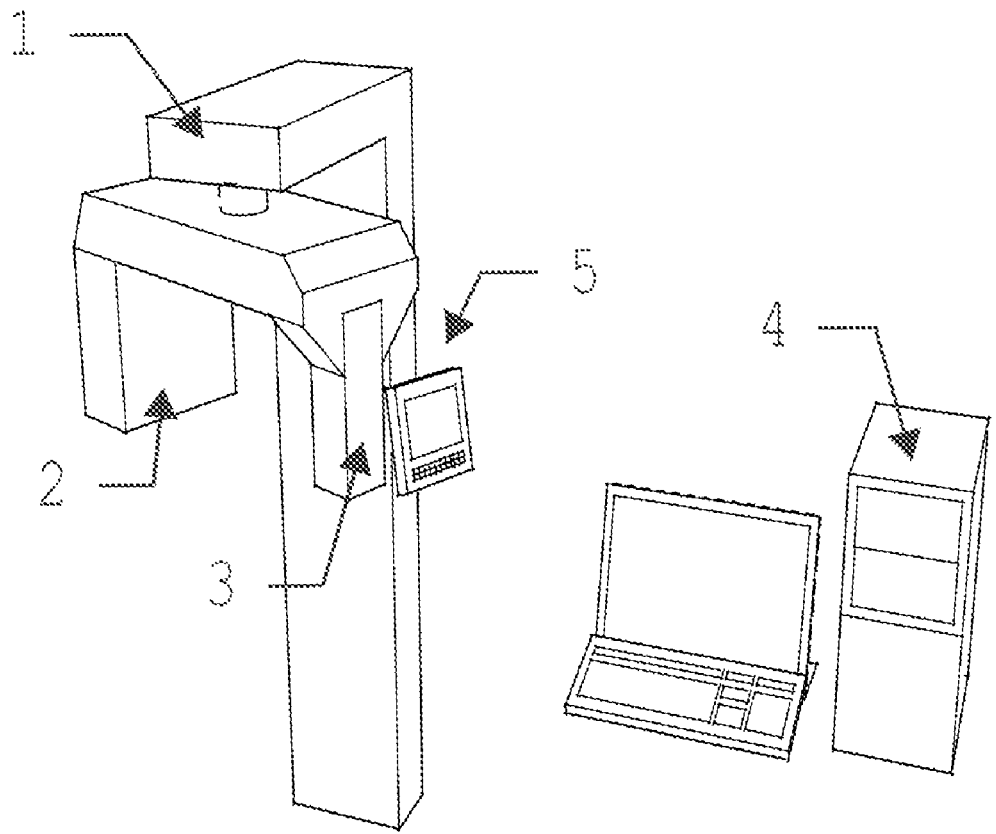
FIG. 1a, is a schematic representation of a standard or conventional panoramic x-ray imaging system in accordance with prior art.

In FIG. 1a, a prior art standard panoramic x-ray imaging system is shown. A column (1) supports the pi shaped assembly with the x-ray tube (2) on one end and the CCD, line output CCD sensor (3) on the other. A manipulator inside the column (1) controls the movement of the assembly of the x-ray tube (2) and the CCD sensor (3). The manipulator usually comprises one or more motors. Normally, there are one or two motors and, in rarely, three motors. A control panel (5) is used to input the required x-ray exposure values (kV, mA) as well as choose the panoramic profile. The image is output, with a digital connection to a personal computer (4).

Figure 1B:
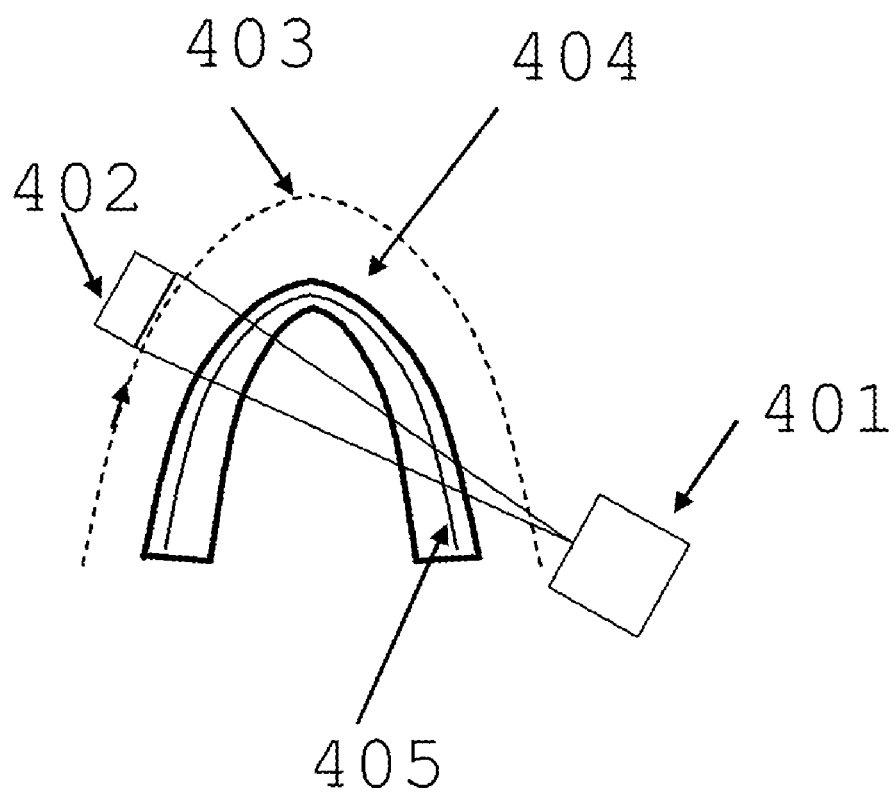
FIG. 1b, is a schematic representation of a standard panoramic program corresponding to a standard panoramic exposure profile, showing the path along which the x-ray source and the imaging device are moving in accordance with the prior art.

The components of a standard panoramic imaging profile in the prior art are illustrated in FIG. 1b. The x-ray source (401) and the imaging device (402), usually a CCD sensor, rotate and translate in order to produce an image of the default focal layer (trough) (405), such movement being along the specified trajectory (403). The aim of this profile (403) is to form a planar image of the ideal or default focal layer (405). The depth resolution varies along the planar image, but is of the order of 30 millimeters at the beginning and the end (molars) of the exposure and is the best, of the order of 3 millimeters, in the mid part (404) (anterior teeth).

Figure 2A:
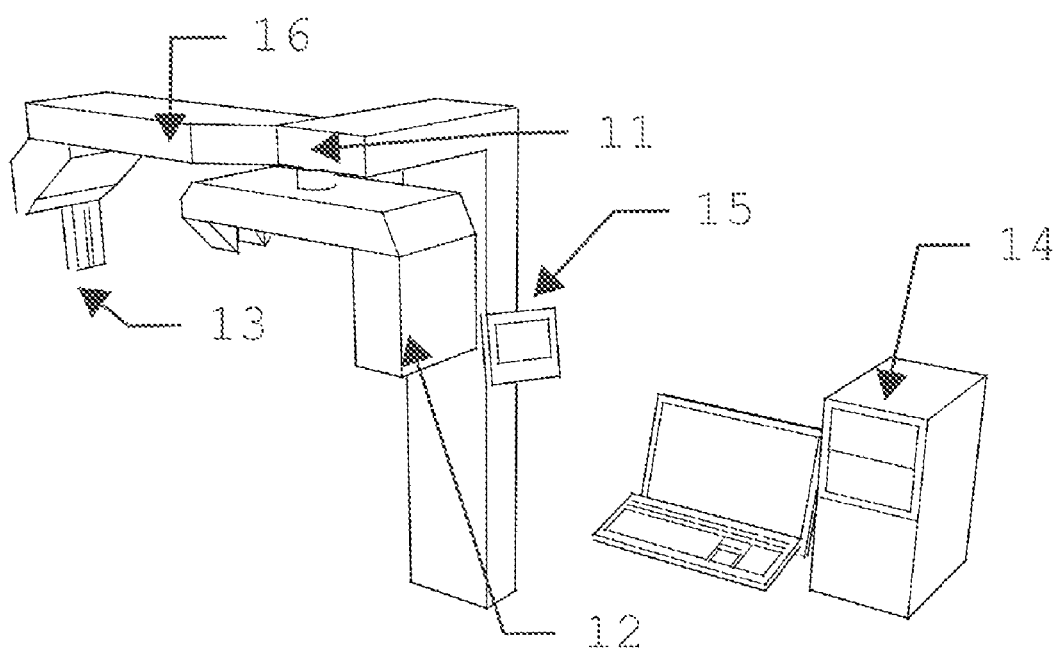
FIG. 2a, is a schematic representation of a standard or conventional panoramic x-ray imaging system including a ceph arm in accordance with prior art.

FIG. 2a, shows schematically a prior art extra-oral dental x-ray imaging system, which combines panoramic imaging as well as the well known cephalometric imaging. The components of such a system are x-ray source (12), imaging sensor device (13) and mechanical manipulator (11) including a "ceph arm" (16), user controls (15) and a computer or processor (14) to process and display the images. The imaging sensor device (13) can move between the cephalometry position (FIG. 2a) and the panoramic position (FIG. 1a) and is commonly referred to as a "snap-on" sensor.

Figure 2B:
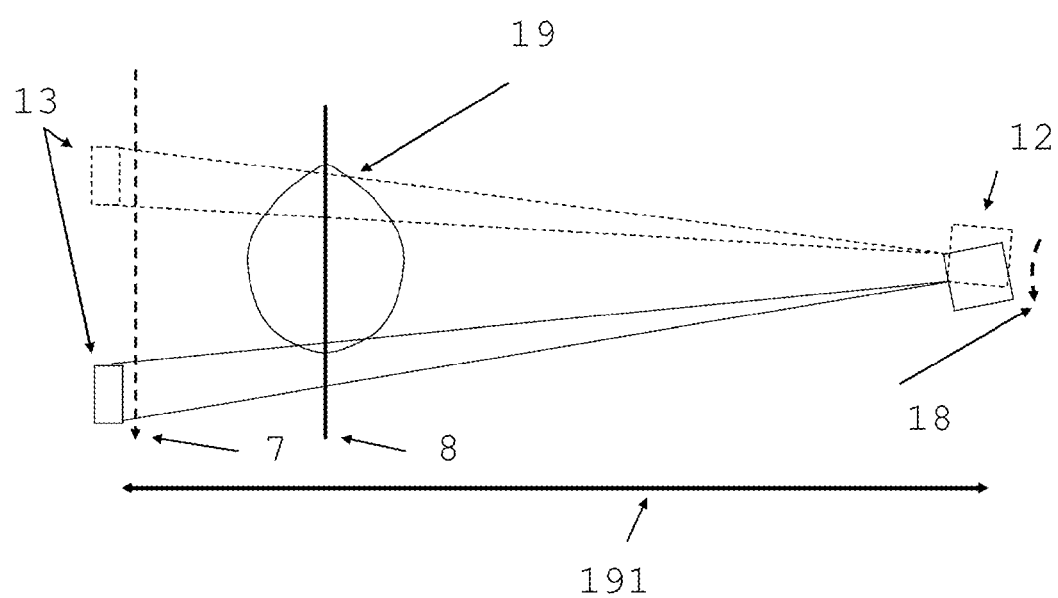
FIG. 2b, is a schematic representation of a standard ceph program corresponding to a standard ceph exposure profile, showing the path along which the x-ray source and the imaging device are moving in accordance with the prior art.

A standard scanning digital cephalometric system in the prior art operates with an exposure profile as illustrated in FIG. 2b. The x-ray source (12) translates and rotates along a predefined path, profile, (18) while the imaging device (13) moves along path, profile, (7) while imaging the patient (19) to form a semi or substantial linear projection of the whole skull across the plane (8). The distance from the focal spot of the x-ray source to the imaging device (191) is large to reduce the geometrical distortion and is in most cases more than 1.5 m (one and a half meters) and typically between 1.5 m-2.5 m. Additionally, the sensor is positioned in a separate "ceph" arm (16) (FIG. 2a) which extends laterally and occupies a lot of space. This large distance is needed so as the x-rays are parallel or almost parallel in order to avoid or mitigate geometric distortion due to the different magnification of the various parts of the object imaged.

Figure 3A:
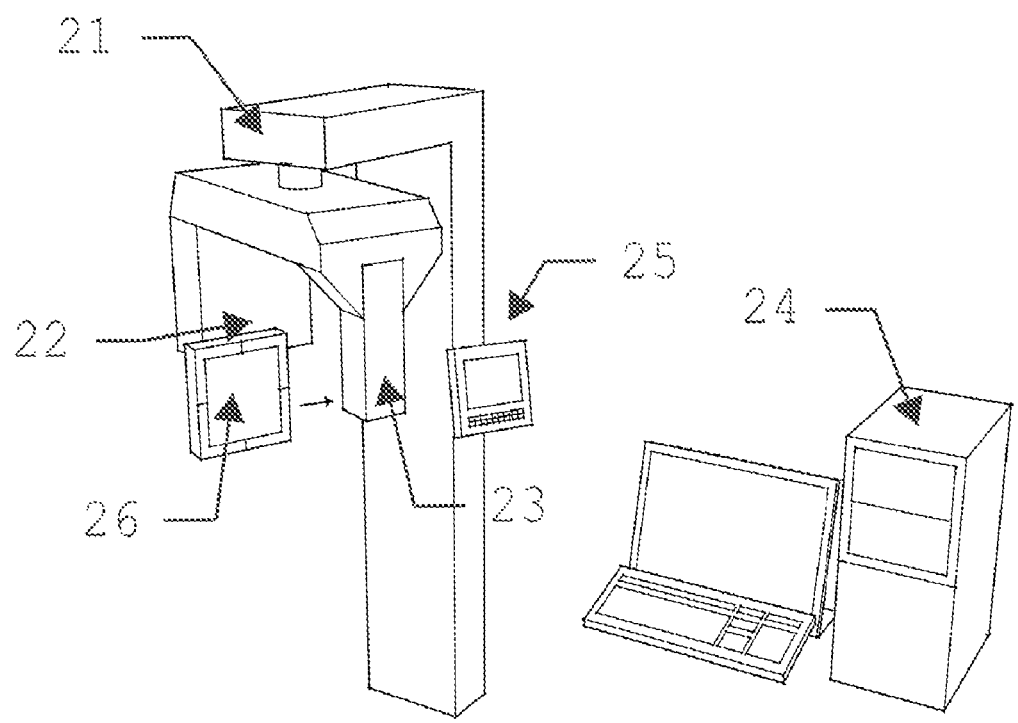
FIG. 3a, is a schematic representation of a standard or conventional panoramic x-ray imaging system or dental CT x-ray imaging system including a second or separate flat panel sensor in accordance with prior art.

In prior art there are also dental extra-oral x-ray imaging systems with a second sensor which is a square flat panel or just one sensor which is a square flat panel. Such a dual sensor system is shown in FIG. 3a, and it is intended for producing transverse slices and/or dental CT images. The column (21) supports as before the pi shaped assembly of the CCD panoramic sensor (23) and the x-ray tube (22). The CCD panoramic sensor (23) can be exchanged with a square flat panel sensor (26). The manipulator inside the column (21) has one, two or three motors usually and shifts in x,y as well as rotates the assembly. A controller, usually digital, (25) sets or selects the kV, mA range as well as selects the various profiles, i.e., movement paths. A computer or processor (24) is provided to process and display the images.

Figure 3B:
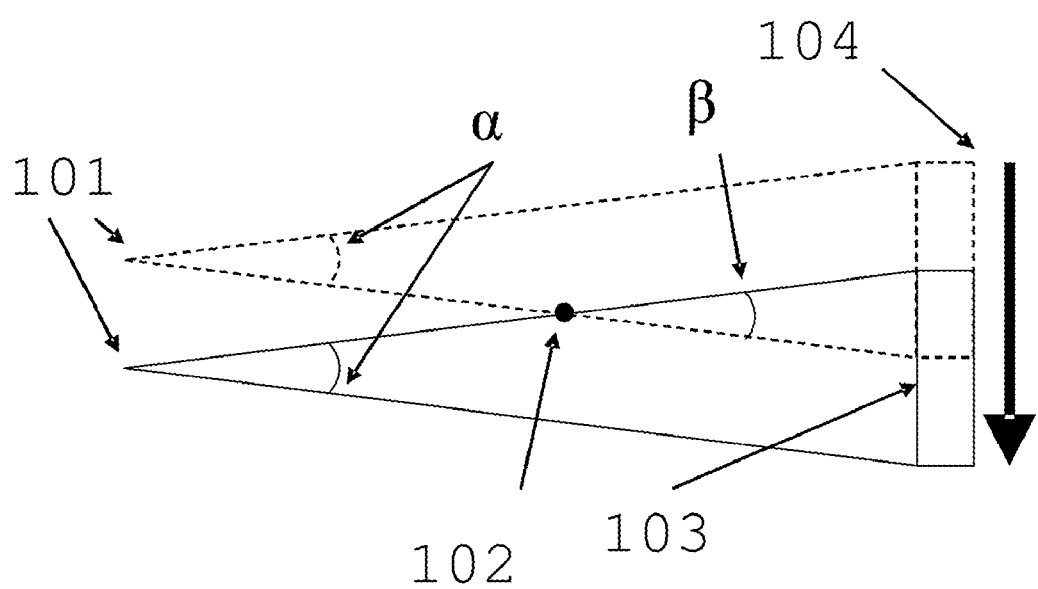
FIG. 3b, is a schematic representation of a standard flat panel program in a dental extra oral imaging system, corresponding to a standard transverse exposure profile, showing the linear path along which the x-ray source and the flat panel imaging device are moving in accordance with the prior art.

FIG. 3b illustrates the classic profile for producing a transverse slice, with an extra-oral dental imaging system utilizing a flat panel in accordance with prior art, namely substantially linear movement. The figure shows the geometry in the horizontal, XY-plane. The movement could have a component also in the z-direction (perpendicular to the XY-plane in the figure), but the basic idea remains the same. In this case the angular viewing range $\beta$, of a point to be imaged (102), is equal to the aperture angle ($\alpha t$) of the sensor, i.e., $\alpha=\beta$, or in other words $\beta/\alpha=1$. The figure illustrates the x-ray source (101), the imaging device in a first position (103), the point to be imaged (102) and the movement trajectory of both the x-ray source and the imaging device in a second position (104) which as can be seen is linear. The solid line refers to the geometry after the movement and the dashed line before the movement. Due to the large size of the typical square flat panel, the viewing angle $\beta$ satisfies the relationship given above. The size of a typical flat panel can be 10 cm×10 cm or 20 cm×20 cm. In the case of a 20 cm×20 cm flat panel and with a distance of the focal spot to the flat panel been typically 50 cm, it means that $\beta/\alpha=1$ and $\beta=\alpha=2\times\tan^{-1}(10/50)=22.6$ degrees. This viewing angle is plenty enough to produce transverse or angled slices of thickness 0.5 mm–3 mm which is considered a very good resolution in the depth direction for a transverse slice. So in the case of profiles with linear movement, utilizing flat panels, $\beta/\alpha=1$ always, and since flat panels are large the viewing angle $\beta$ is usually large enough to produce transverse slices sufficiently thin. The problem to be solved, however, is the following: a) flat panels are expensive, b) although flat panels can make good transverse slice images they unfortunately produce panoramic images of poor resolution. This is reason why systems that aim to offering both panoramic as well as transverse slice profiles, have two sensors which adds to the complexity and cost of the extra-oral dental imaging system.

Figure 3C:
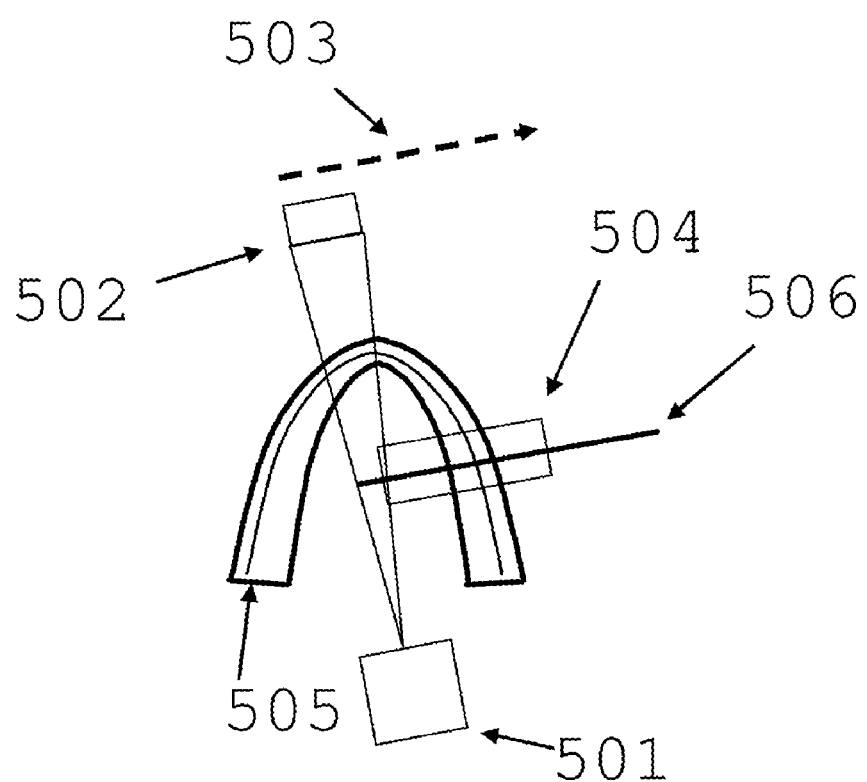
FIG. 3c, is a schematic representation of a standard flat panel program in a dental extra oral imaging system, corresponding to a standard transverse exposure profile of the prior art, showing the mostly linear path along which the x-ray source and the flat panel imaging device are moving in accordance with the prior art.

FIG. 3c shows the standard transverse slice exposure profile as is known in the prior art by means of using a flat panel detector with length m and width n. Such flat panels have a relationship of m/n substantially equal to one (i.e., m/n=1). Usually a flat panel performs a linear scan where $\beta/\alpha=1$. There are cases that the flat panel size may be 10 cm×10 cm or as small as 5 cm×5 cm. In such cases there is a series of linear scans allowing for a wider viewing angle. This is shown in FIG. 3c. In accordance with prior art as illustrated in FIG. 3c the x-ray source (501) and the imaging device (502) perform a substantially linear translation around the region of interest (504). The trajectory or profile (503) suffices to form a planar image (506) which is a transverse slice across the default focal layer (505).

In any case, even in the smallest panels with dimension 5 cm×5 cm, the angle $\alpha=2\times\tan^{-1}(2.5/50)=5.7$ degrees. In order to have a nominal transverse slice thickness of 0.5 mm to 3 mm the viewing angle $\beta$ should be 10 degrees or more.

This would mean that $\beta/\alpha=10/5.7=1.8$ Therefore in all known cases transverse slice imaging is performed with a square or near square flat panel with m/n≈1 and with movement profiles identified with these parameters of $\beta/\alpha\leq1.8$, one is obtaining in the prior art transverse slices with adequate thickness resolution. The same set-up is or can be used for performing volumetric 3D imaging. The problem is however that one is still engaging one sensor for performing panoramic imaging, typically a CCD line output sensor, and a second sensor, a flat panel with m/n approximately equal to one, for doing one or more linear scans satisfying the relationship $\beta/\alpha\leq2.6$.

Figure 4:
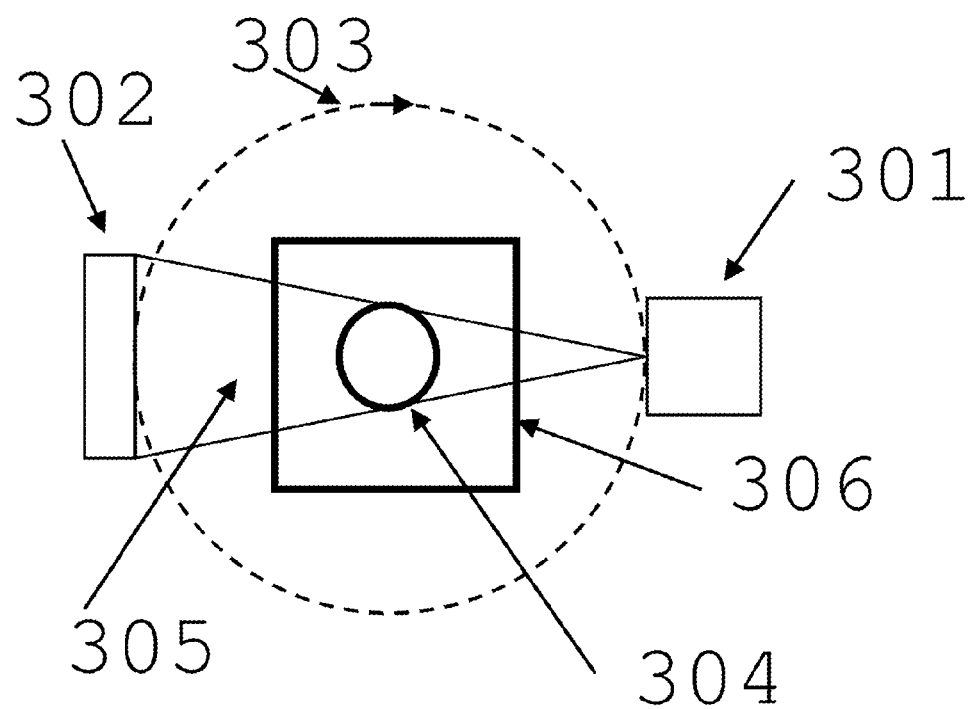
FIG. 4, is a schematic representation of a standard flat panel dental CT program corresponding to a standard dental CT exposure profile, showing the path along which the x-ray source and the flat panel imaging device are moving in accordance with the prior art.

A schematic representation of a standard extra-oral dental volumetric x-ray imaging system geometry and movement is illustrated in FIG. 4. The aim is here to produce a 3D volume. The x-ray source (301) and the flat panel imaging device (302) with m≈n rotate along a given (circular) path (303) while multiple images of the region of interest (304) are captured from the projection (305). These images are then used to reconstruct the conventional horizontal tomographic slice (306) which contains the region of interest. The region of interest is divided into smaller volume elements, voxels. The size of a voxel can be chosen independent of the pixel size of the imaging device. Normally the voxel is isotropic, i.e., the width and height of the voxel are equal, i.e., the voxels are square, but the voxel can also have unequal dimensions. Normally the trajectory (303) is a circular rotation with at least 180 degree angular viewing range. Also every point in the region of interest should be seen in every image taken during exposure. This means that the size of the region of interest is limited by the size of the imaging device.

If the condition that the angular viewing range $\beta$ is at least 180 degrees is fulfilled, a "perfect" or optimal volumetric reconstruction can be obtained.

Application Ser. No. 11/277,530, discloses an x-ray imaging system where a frame output sensor is used with m/n>1.5. The sensor is a panoramic sensor and the teaching of that invention is to use such a sensor with m/n>1.5 in a extra-oral dental x-ray imaging system, so that with a single exposure along the profile suitable to produce a panoramic layer one would obtain additionally to the panoramic layer one of: a) transverse slice or b) a 3D volumetric image. Therefore Ser. No. 11/277,530 teaches a single extra oral system with a single sensor and a single profile or exposure. However in practice the panoramic profile is such that the x-rays come almost parallel to the transverse slice direction, and from such panoramic profile is extremely difficult or impossible to produce a transverse slice and even more difficult to make a 3D volume.

The problem to be solved therefore is to provide an inexpensive extra-oral dental imaging system with a single sensor that is capable of producing at least two of a) good quality panoramic images, b) good quality angled or transverse slice images, c) good quality cephalometric images without the use of an additional "ceph" arm, and d) good quality local 3D volumetric images.

The inventors of the current invention have discovered that an inexpensive, linear sensor with frame output mode can be used to produce a transverse slice with good quality if a second profile is implemented that translates and rotates the m/n≥1.5 frame mode sensor along a profile path, such profile defined by a suitable relationship of $\beta/\alpha$.

Figure 5:
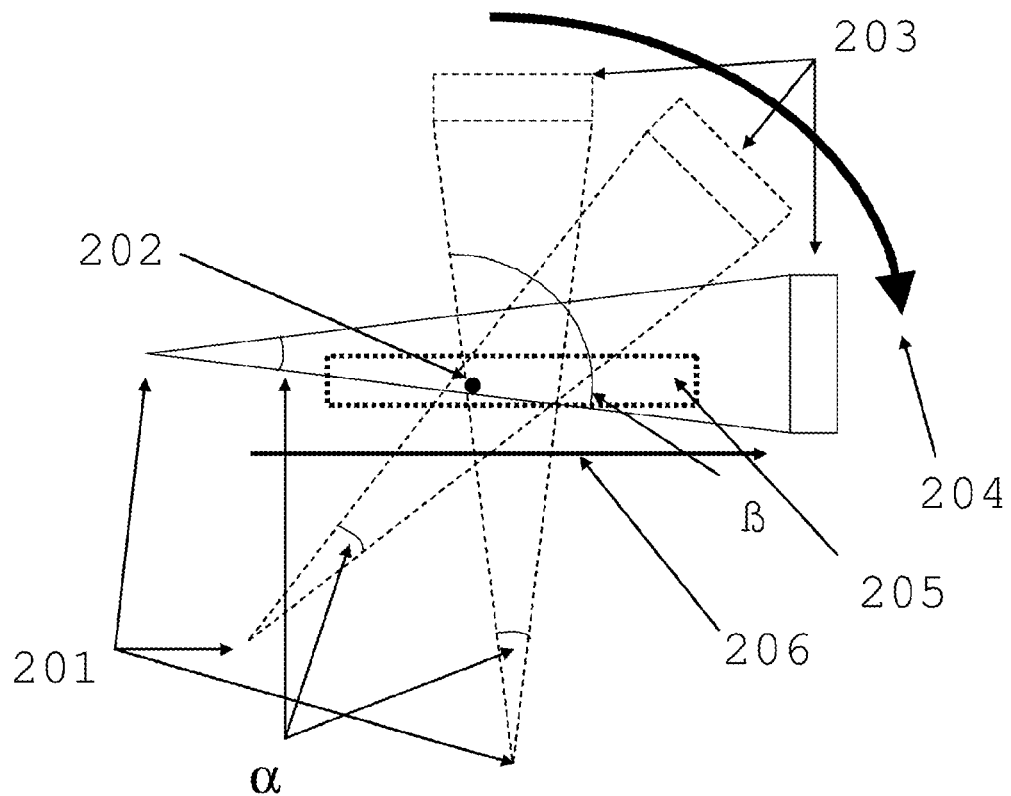
FIG. 5 is a schematic representation showing the relationship of angles $\alpha$ and $\beta$ in accordance with the current invention.

One aspect of the current invention is illustrated in FIG. 5. The sensor (203) is preferably a CdTe-CMOS or CdZnTe-CMOS linear sensor with preferably long dimension m and short dimension n, where typically m≈150 mm and n≈6 mm, i.e., m/n≈25. Other linear type of sensors with different than CdTe materials can be used. The sensor is working in frame output mode providing typically 50 fps-500 fps. The focal spot of the x-ray source is (201) and is typically at a distance of 300 mm to 600 mm from the sensor. Therefore in this configuration the angle $\alpha$ is in the range of 0.5 degrees to 1.1 degrees, i.e., including the end points 0.5 and 1.1. In order to obtain good transverse slices, or slices at an angle to the panoramic layer, or a local 3D volumetric image of a region of interest, one should have viewing angles in the range of 10 degrees-15 degrees or more, including the endpoint of 10 degrees. Therefore the ratio $\beta/\alpha$ is at least 15/1.1=13.6, since the preferable viewing angle range is $\beta$=15 degrees.

With a profile defined with this ratio, the extra-oral imaging system is able to operate on a single linear and inexpensive sensor and perform both panoramic and transverse or angled slices with good resolution, with layer thickness of less than 5 mm, preferably will be less than 3 mm and more preferably will be less than 2 mm. The term "layer thickness" has the meaning of the physical area which is considered to be in focus, ie an object contained within the "layer thickness" will be imaged with sufficient sharpness or clarity while objects outside the "layer thickness" will be blurred. Robustly one measures the sharpness or the blurriness with the Modulation Transfer Function (MTF) and for example an MTF of 0.1 (zero point one) or more would indicate a sharp or in-focus image. The region of interest (205) may contain one or several layers.

In another embodiment CdTe-CMOS sensor (203) has m≈150 mm and n≈25 mm, i.e., m/n≈6. In such case if the distance between focal spot (201) and sensor (203) is again in the range 30 mm to 600 mm, $\alpha$ is in the range of 2.3 degrees and 4.7 degrees, including the endpoints of 2.3 and 4.7 degrees. If $\beta$ is at least 10 degrees then $\beta/\alpha$ is at least 15/4.7=3.2

In a third embodiment the sensor length m can be 50 mm-100 mm and the width n≈25 mm, i.e., m/n≈1.5 or more. In such case $\alpha$ is in the range again 2.3 degrees 4.7 degrees, including the endpoints of 2.3 and 4.7 degrees. Again this would mean that the relationship of $\beta/\alpha>3.2$ defines a profile that would be suitable for good quality panoramic and transverse or angled to the panoramic slices or a local 3D volumetric image of a region of interest. One is able to achieve satisfactory transverse slice or angled slice thickness even with $\beta$=10 degrees or more in which case $\beta/\alpha>2.1$ in accordance with the current invention.

The angled slice profile or transverse exposure profile or a local 3D volumetric image exposure profile defined above can be used in at least one region of interest in a panoramic layer, but can also be used for each anatomical region of interest, such as the molar and anterior teeth regions individual teeth or teeth within a region. An extra-oral dental x-ray imaging system in accordance with the invention provides such angled slice or transverse exposure profiles with respect to the standard panoramic layer.

To achieve this relationship of $\beta/\alpha>2.1$ (at least), a substantial rotational component is added by the inventors to extend the angular viewing range, $\beta$, beyond the limit of the sensor's aperture angle $\alpha$. This is illustrated in FIG. 5, which shows how substantial rotation is used to increase the viewing angle $\alpha$. In that figure, the x-ray focal spot (201) and the imaging device (203) rotate and translate along the specified trajectory (204) while imaging a point (202) of the region of interest (205). The angular viewing range $\beta$ is therefore much larger that the aperture angle $\alpha$, since $\alpha$ is actually quite small as shown above for a linear or near linear sensor with m/n>1.5. The aim of the imaging process in this case is to form a planar image along the dimension of arrow (206). While prior art systems require a flat panel sensor, which is essentially square, as well as a second linear sensor with a line output, the current invention overcomes the obstacles of the prior art and provides a system capable with a single sensor such sensor operating in frame output mode and with m/n>1.5, said extra oral system further programmed to have at least two profiles, one for a panoramic layer/image and a second profile for doing a transverse or angled slice, said second profile defined by $\beta/\alpha>2.1$. Therefore the extra-oral dental x-ray imaging system is multifunctional and economic.

With increased angular viewing range, i.e., $\beta/\alpha>2.1$ the depth resolution is improved, i.e., smaller objects can be better resolved in the depth direction. The larger the angular viewing range $\beta$, the better the depth resolution.

The same extra oral system as disclosed in the invention is suitable for performing a local 3D volumetric image. One algorithm for executing angled slice imaging and/or local 3D imaging is provided herein with reference to FIGS. 6a and 6b.

One downside of the substantial rotation angle $\beta$ is that the direction of x-rays becomes close to parallel to the direction of the planar image (angled slice) which causes geometrical distortion in the image if using standard algorithms designed for planar imaging. Such prior art algorithms are the same used in the reconstruction of panoramic layers, and they may be referred to as laminography or tomosynthesis. The current invention provides an extra-oral dental imaging system and an algorithm how to optimally obtain a transverse or angled slice to the panoramic layer.

Figure 6A:
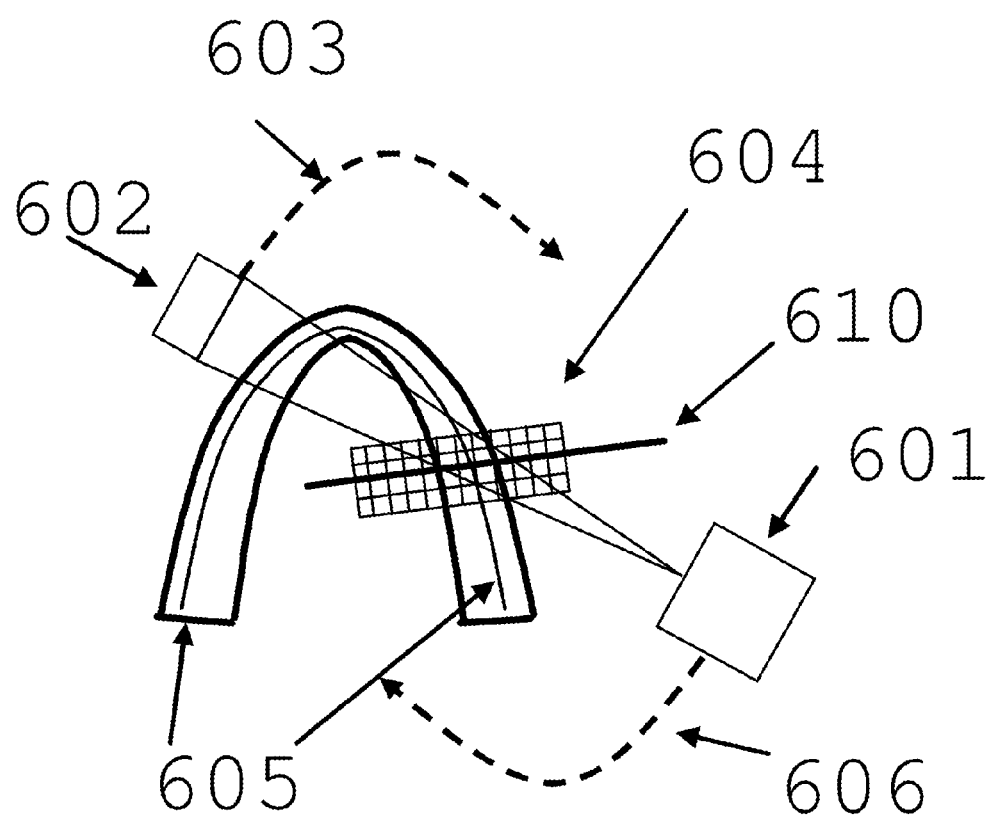
FIG. 6a is a schematic representation of the transverse program, corresponding to the transverse exposure profile for a volume of interest for producing a transverse slice image in accordance with the current invention.

The current invention provides an extraoral dental imaging system and an algorithm that combines the planar and volumetric imaging modalities to form a planar image with better depth resolution along the direction z, without the need to calculate a full volumetric image, which would need a wide expensive sensor. Additionally a local 3D volumetric image can be formed from the distinct planar layers. FIG. 6a shows the x-ray source (601), the imaging device (602) moving along trajectory (603), (606) in accordance with the current invention. The default panoramic layer is (605). As shown in FIG. 6a, the angled slice of preference (610) is at right angles with the panoramic layer in the region of interest (604). In many cases the angled slice can be approximately at right angles with the panoramic layer but preferably 90 degrees±20 degrees. In certain implant operations the angle of the slice can be different from the transverse direction.

Figure 6B:
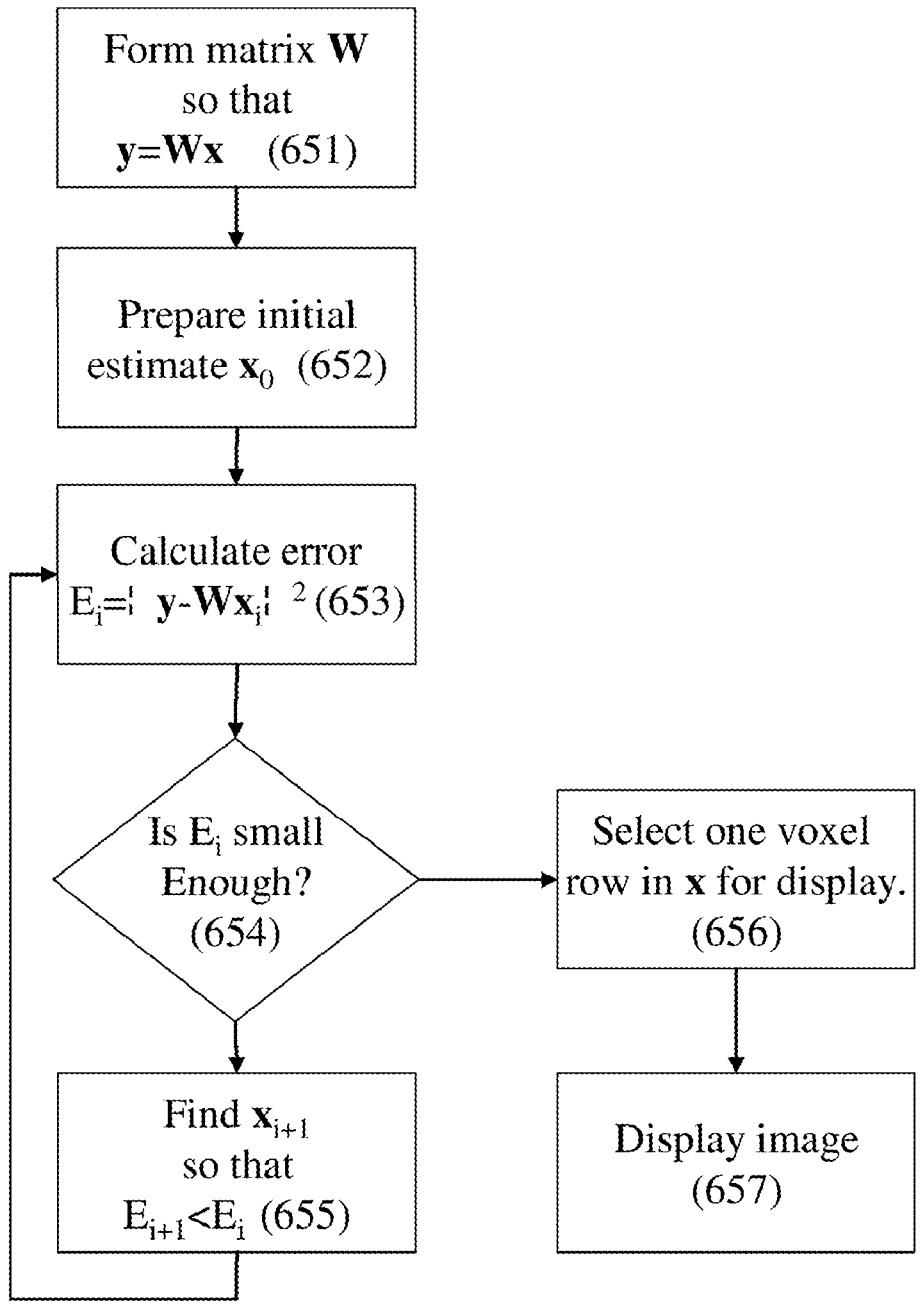
FIG. 6b is a flow chart of an algorithm used by a processor for reconstructing a transverse image from the frames produced by the imaging device in a dental extra-oral x-ray imaging system in accordance with the current invention.

In accordance with the current invention, in order to form a transverse or angled slice (610), the following algorithm in accordance with FIG. 6b is applied.

The algorithm is applied to each horizontal tomographic slice separately and the final image, which is a transverse slice or an angled slice, is formed by stacking the selected region of interest in each horizontal tomographic slice vertically.

Definitions:
x a vector of voxel values. For each voxel there is exactly one value in the vector.
y vector of projections. Each pixel in every projection (frame) has exactly one element in the vector. The values correspond to values of said pixels in the projections.
W matrix of weights. This matrix encodes the geometry of the system so that the projection equation can be expressed in form y=Wx First step (651) in the algorithm is to form weight matrix W. The matrix has one row for every pixel in every projection (thus the total number of rows is number of projections x number of detector pixels in one horizontal tomographic slice.). The matrix has one column for every voxel value (i.e., the number of columns in the number of voxels in x). Each element in the matrix indicate how much the corresponding voxel contributes to said pixel value of said projection. This step is usually performed on the calibration of device and is not calculated during a normal exposure.

Second step is to prepare an initial estimate x0 (652) ("guess") for voxel values x. The initial estimate can be calculated, for example, using the classing shift-and-add algorithm for tomosynthesis. The quality of the initial estimate does not affect substantially the quality of the reconstructed image, but a good initial estimate allows shorter processing times. The third step (653) is to evaluate the current value for x. This is done by calculating suitable mathematical error norm, such as sum of squared differences.

The fourth step (654) is to decide whether the error is small enough. If the error is sufficiently small, then the loop is ended and the image is finalized in the sixth step.

The fifth step (655) is to calculate a new estimate for x so that the error norm is decreased. This can be calculated for example by the well known gradient descent algorithm. After this the algorithm continues at the third step.

The sixth step (656) is to select one voxel row in x to be displayed as one row in the final image. There is usually one row that has the best image quality depending on the geometry of the device. Additionally combining the voxel rows one can form a local 3D image.

The seventh and last step (657) is to display one row of the final image, such image being a transverse or an angled slice.

In accordance with yet another aspect of the current invention, there is provided an extra-oral dental imaging system capable of cephalometric, i.e., substantially linear, projections without the need of an external long arm. This system offers unique advantages over prior art, such advantages been the utilization of a single sensor to perform panoramic as well as cephalometric projections without the expensive external arm.

A schematic representation of the prior art cephalometric imaging system is given in FIG. 2a. The components of such a system are x-ray source (12), imaging device (13) and mechanical manipulator including a "ceph arm" (16), user controls (15) and a computer or processor (14) to process and display the images. FIG. 2b has been already described and shows a typical profile movement of the conventional ceph system shown FIG. 2a.

Figure 7:
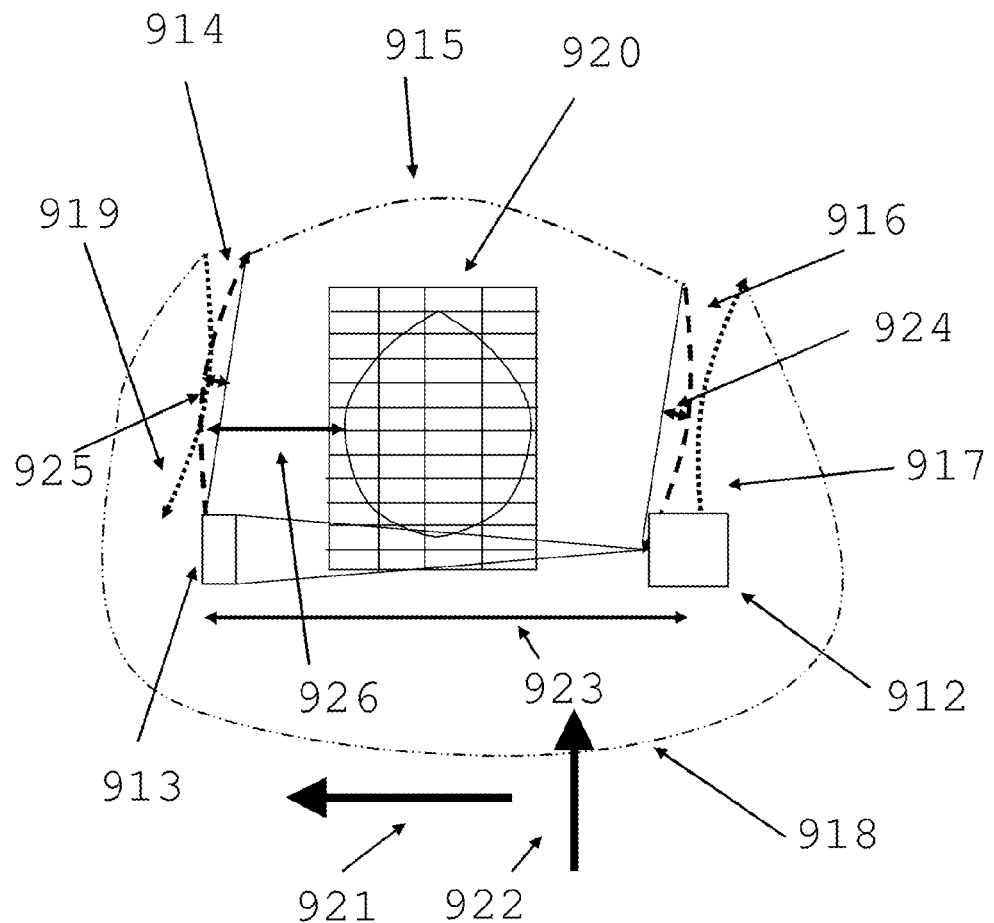
FIG. 7 is a schematic representation of the near linear projection program, corresponding to the linear exposure profile for producing a linear projection image of at least part of a human skull in accordance with the current invention.

According to the invention the cephalometric functionality, or cephalometric profile movement, of a multipurpose extra-oral dental x-ray imaging system operates as illustrated in FIG. 7. A cephalometric projection, which is a linear projection of the human skull, is achieved by one or more linear or substantially linear exposure profiles with the use of a single sensor which is positioned with respect to the x-ray source in the same location as during the execution of the panoramic exposure profile. The distance (923) between the focal spot of the x-ray source (912) and the imaging device (913) must be less than 1.5 m and preferably should be less than 70 cm, in order to be able with the same fixed sensor and fixed geometry to perform also panoramic imaging. Therefore the cumbersome "ceph" arm is eliminated and a simple, compact multifunctional extra oral imaging system is achieved. The x-ray source (912) executes a profile program along trajectory (917,918,919) and the CdTe-CMOS x-ray and frame output sensor (913) moves along the trajectory (914,915,916) to form a highly anisotropic volumetric image of the region of interest (920). As mentioned above the distance from the x-ray source to the imaging device is small compared to the standard case. The distance (926) between the sensor (912) and the nearest face of the skull to the sensor is minimized or ideally reduced as much as reasonably feasible during each of the exposure linear profiles. In this way one side of the skull is projected with minimum blurring or distortion, while the other is disproportionate and can be corrected or eliminated from the image with further processing. Such distance (926) should be less than 20 cm, more preferably less than 10 cm and ideally less than 5 cm. In accordance with the current invention, the focal spot of the x-ray source to imaging device distance (923) is short compared to prior art solutions. (923) is preferably less than 1.5 m and even more preferably in the range of 30 cm-70 cm, which is the range used for panoramic imaging. Therefore with one mechanical arrangement the current invention accomplishes both panoramic and cephalometric imaging. This saves a lot of equipment space and mitigates the need for multiple or removable sensors.

The voxels in the volumetric image of the region of interest (920) have a small size in the imaging dimension (922), but large size in the perpendicular dimension (921).

The trajectories of the x-ray source and the imaging device are divided into 3 segments: The first exposure (914, 917), the non-radiating movement (915, 918) during which the x-ray source (912) and the sensor (913) reposition and the second exposure (916, 919). During the two exposure parts the left and right side of the skull are imaged. The two parts of the profile during which the skull is exposed to radiation are linear or substantially linear as seen in FIG. 7. Substantially linear section means that the distance (924) and (925) of the bow to the arch is less than 20 cm, preferably less than 10 cm and even more preferably less than 1 cm. A "section" means a part of the trajectory which is more than 5 cm long in length and therefore long enough to produce data that will be used in the reconstruction for an image to be displayed. It should also be noted here that other projection profiles with similar effect can be used. For example an "L" shaped projection profile with two substantially linear sections with a common point. Alternatively one can use only one substantially linear projection and project part or one half of the human skull.

Figure 8A:
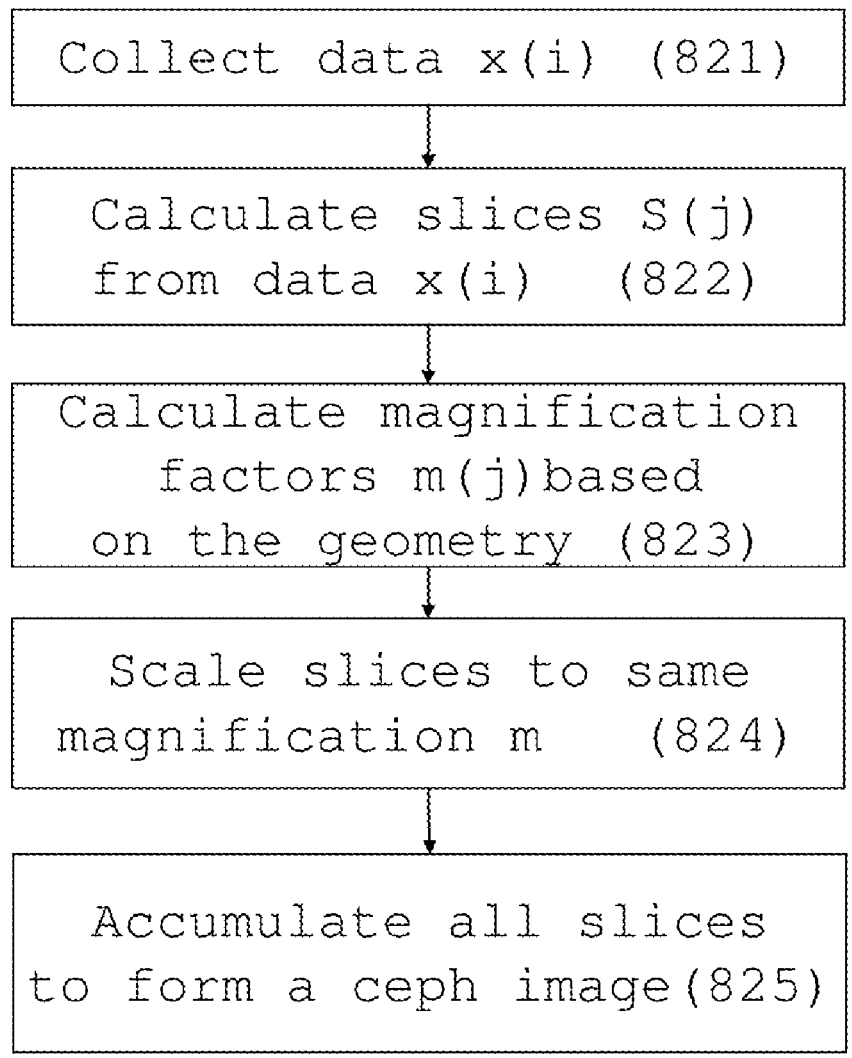
FIG. 8a is a flow chart of an algorithm used by a processor for reconstructing a cephalometric projection image from the frames produced by the imaging device in a dental extra-oral x-ray imaging system in accordance with the current invention.
Figure 8B:
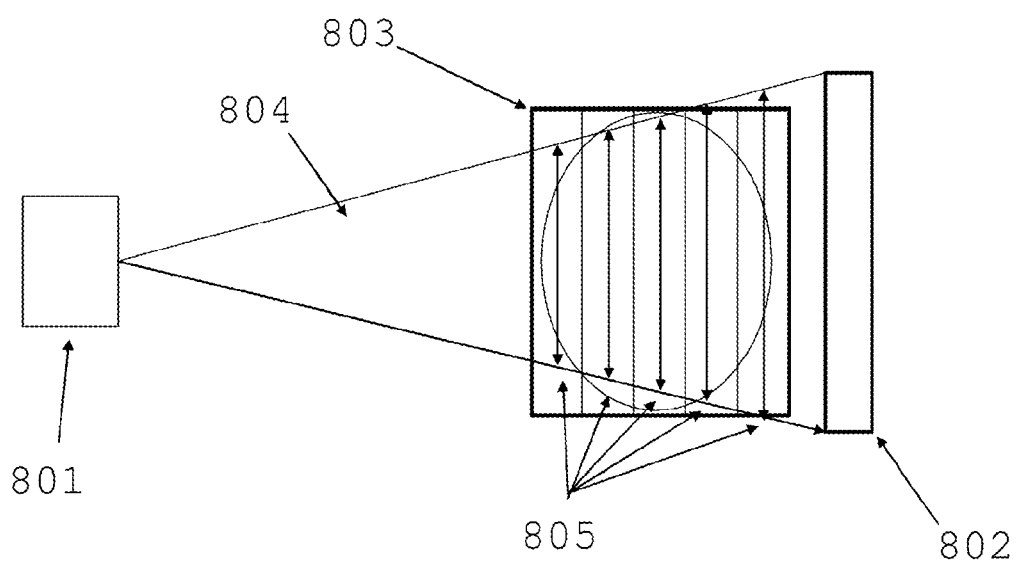
FIG. 8b shows the geometry for data collection in accordance with current invention for obtaining a cephalometric or linear projection.

After the exposures, a volumetric reconstruction algorithm is used to calculate vertical slices along imaging direction (922). These vertical slices are then transformed to eliminate the different magnification factor of different vertical slices. Finally, the vertical slices are added together to produce one two dimensional cephalometric image. Although not limited to any specific reconstruction algorithm, one such algorithm for the reconstruction is represented in FIGS. 8a, 8b and 8c.

First step in the algorithm is data collection (821). In the data collection step multiple frames and corresponding x-ray source and imaging device locations are recorded. The geometry for data collection is illustrated in FIG. 8b. The x-ray source (801) illuminates all the different layers (803) in the object. The x-ray imaging device (802) collects the x-rays and forms an image. The different layers (803) have different magnifications factors because of the shape of the beam (804). The different magnification factors are visualized with the double-headed arrows (805). The arrows closer to the x-ray source are shorter while the arrows closer to the imaging device are longer. The image stored by the imaging device (802) consist of a sum or superposition of all these layers. The next step (822) is to reconstruct the content of each individual layer and form a separate image for each and every layer. The images can be reconstructed for example by using the algorithm described earlier for the transversal imaging. A layer refers here to a plane in the voxel field parallel to the imaging device.

Then the next step (823) consists or calculating the magnification factors for each individual layer image.

Figure 8C:
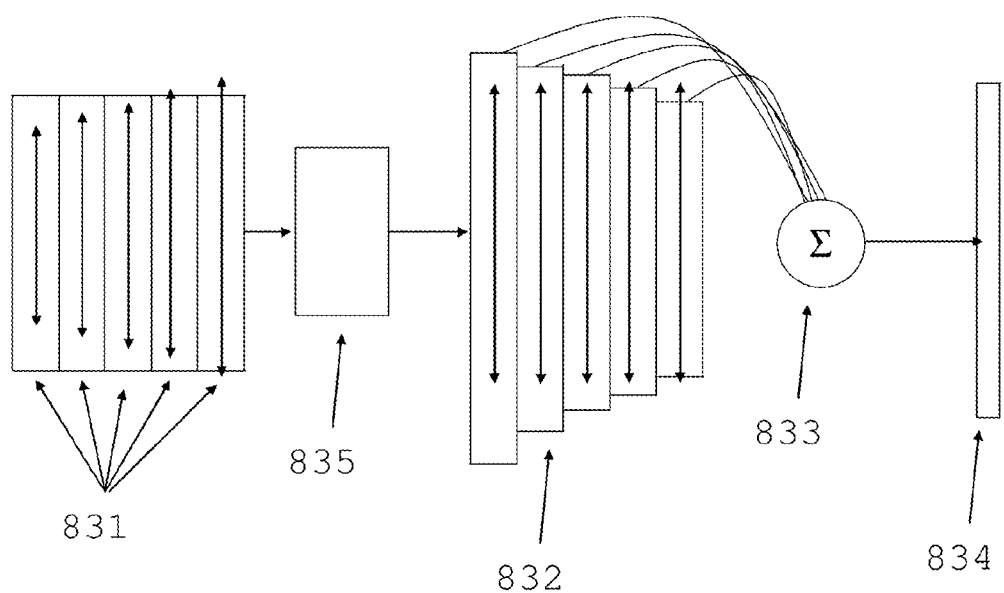
FIG. 8c shows schematically the re-scaling of the layers and addition in order to obtain a cephalometric or linear projection in accordance with the current invention.

Then (824) the individual layer images (831) in FIG. 8c are rescaled by using a rescaling algorithm (835) such as bicubic interpolation so that the magnification factor after rescaling for each individual layer image is the same. After this there are multiple images with different sizes but with equal magnification factor.

The last step (825) is illustrated by FIG. 8c and is to accumulate all the rescaled individual layer images (832) using an adder (833) to form the final image (834) which is now a superposition of all the different layers, but in contrary to the original image data, the different layers have equal magnification factors. Thus the final image is substantially equal to an image taken with a parallel beam x-ray source or equal to an image taken with a normal cone beam x-ray source with large x-ray source to imaging device distance and small object to imaging device distance.

With reference to FIGS. 9b, 10a, 11a and 11b we now describe another preferred embodiment of the current invention.

Figure 9A:
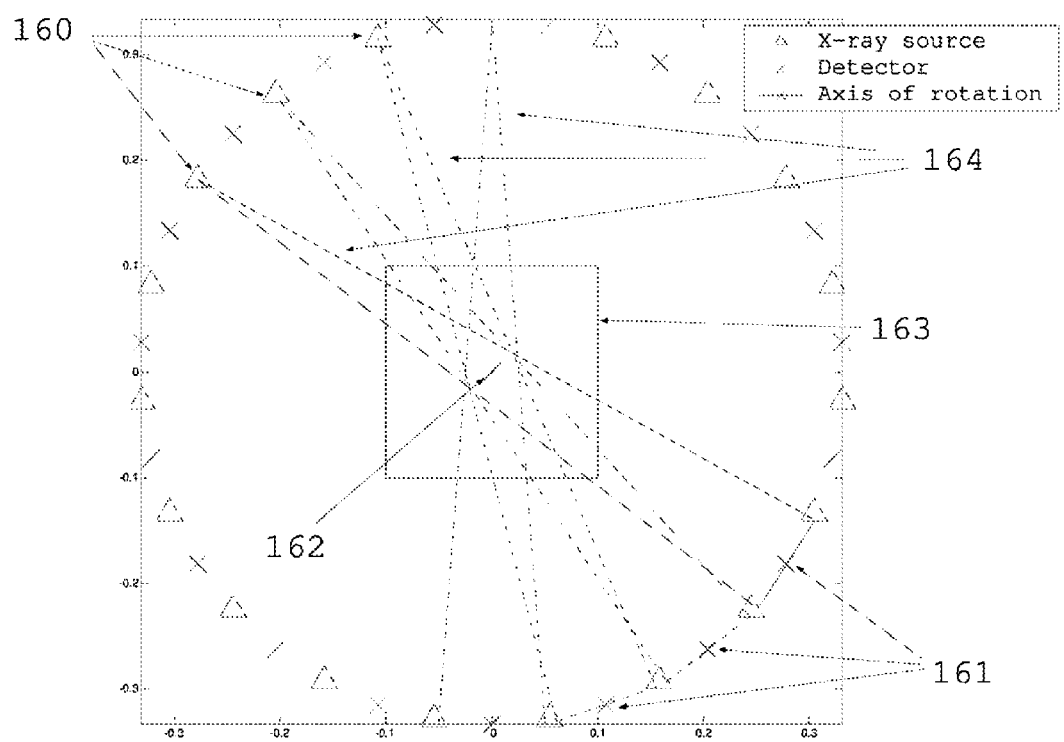
FIG. 9a shows an example reconstrutable region using a stationary axis of rotation in accordance with prior art.

A prior art dental CT or 3D system has movement trajectory of a circle as illustrated in FIG. 9a. Both the x-ray generator(source) (160) and the imaging device (detector) (161) move along a fixed path with a stationary axis of rotation. The system usually rotates 180 to 360 degrees, i.e. half a circle to a full circle. Some example beam projections are given as a reference (164). The axis of rotation (162) is fixed and in the middle of the region of interest (163). For example this is in accordance with prior art as described in U.S. Pat. No. 6,118,842.

This trajectory produces a reconstructed arc of a cylinder which has a circular projection in the horizontal plane. The diameter of this circle is equal to width of the imaging device divided by the magnification factor (assuming 180 degree rotation) or at most equal to twice the width of the imaging device divided by the magnification factor if a so called half-beam technique (involving 360 degree rotation) is used. In normal systems with for example a 5 cm wide detector this would give at most 2*5 cm/2=5 diameter for the reconstructed cylinder assuming a typical magnification factor of 2.

A necessary condition for perfect reconstruction with prior art methods assumes that every point inside the volume to be reconstructed is seen in every projection or that every point inside the volume to be reconstructed is seen in full angular range of 0 to 180 degrees. This allows some points to be unseen in some projections as used in the so called half-beam technique. FIG. 10b illustrates this. A trajectory with a fixed axis of rotation (181) is limited to a reconstructable region (182) that is proportional to the width of the detector regardless of how many frames are collected.

Figure 9B:
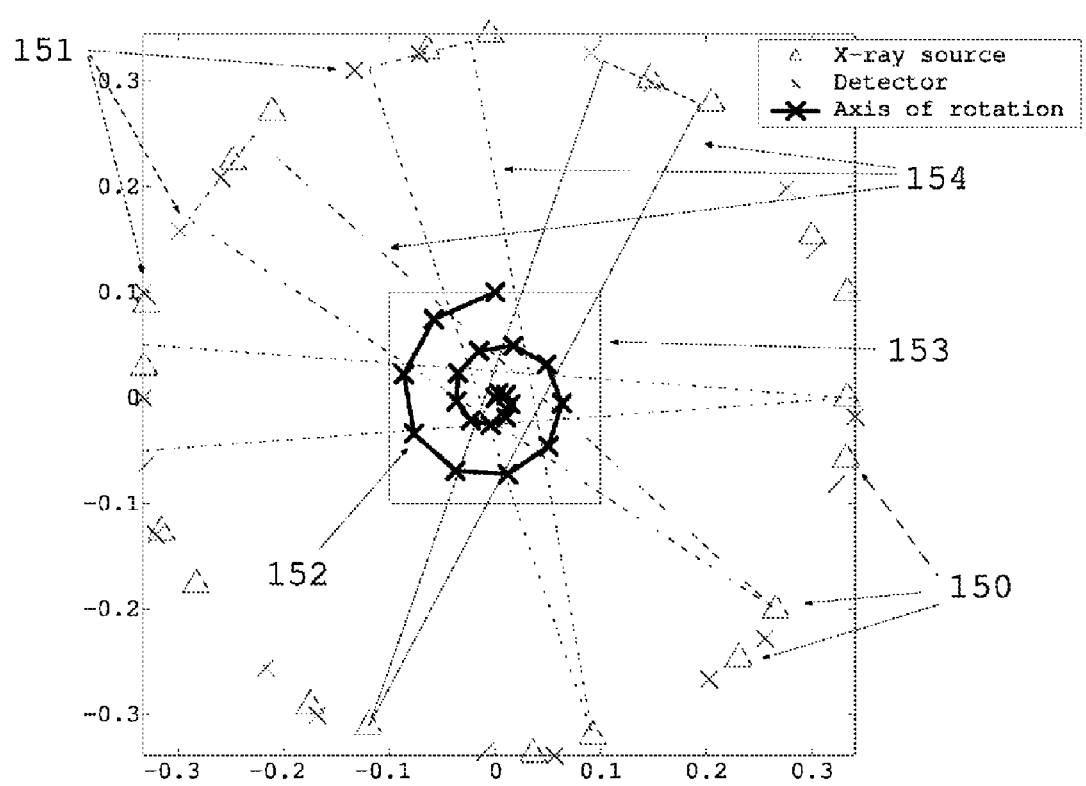
FIG. 9b shows an example reconstructable region using a non-stationary axis of rotation using a spiral path in accordance with the current invention.

In accordance with the current invention there is provided a dental extraoral x-ray imaging system having a mode of operation for panoramic imaging and a mode of operation for partial CT or 3D imaging a region of interest. When in the panoramic mode the system will operate in a panoramic trajectory and when in partial CT or 3D mode the system will operate in partial CT mode characterized in that the axis of rotation is no longer fixed, as is in conventional systems (eg U.S. Pat. No. 6,118,842), but moves as well. By way of a preferred example, the axis of rotation when in partial CT/3D mode is moving along a spiral. An example of a spiral trajectory of the axis of rotation is represented in FIG. 9b. In this figure the x-ray generator (150) and imaging device (151) move along a circular trajectory, but the axis of rotation (152) moves along a path, which in this plot is a spiral. Other trajectories of the axis of rotation are possible without departing from the scope of the invention. The region of interest (153) and sample beam projections (154) are given as references.

Figure 10A:
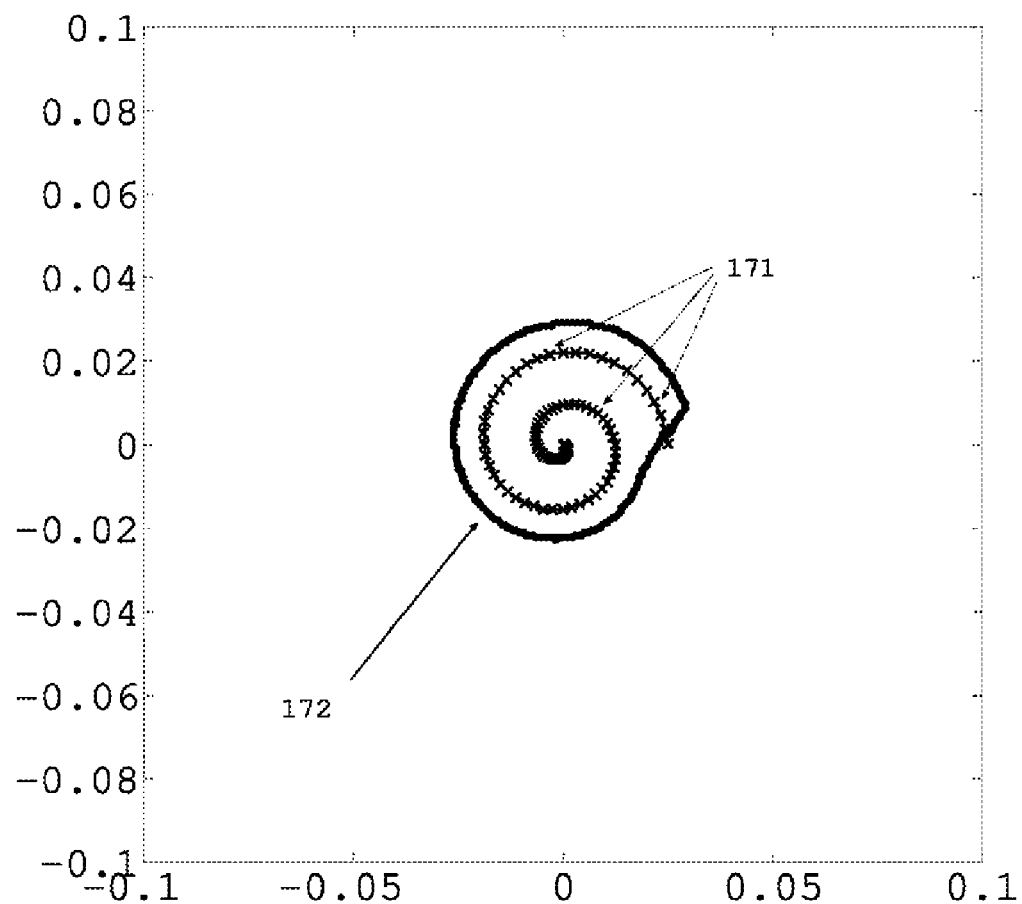
FIG. 10a shows an example of the size of the reconstructable region in accordance with the current invention.
Figure 10B:
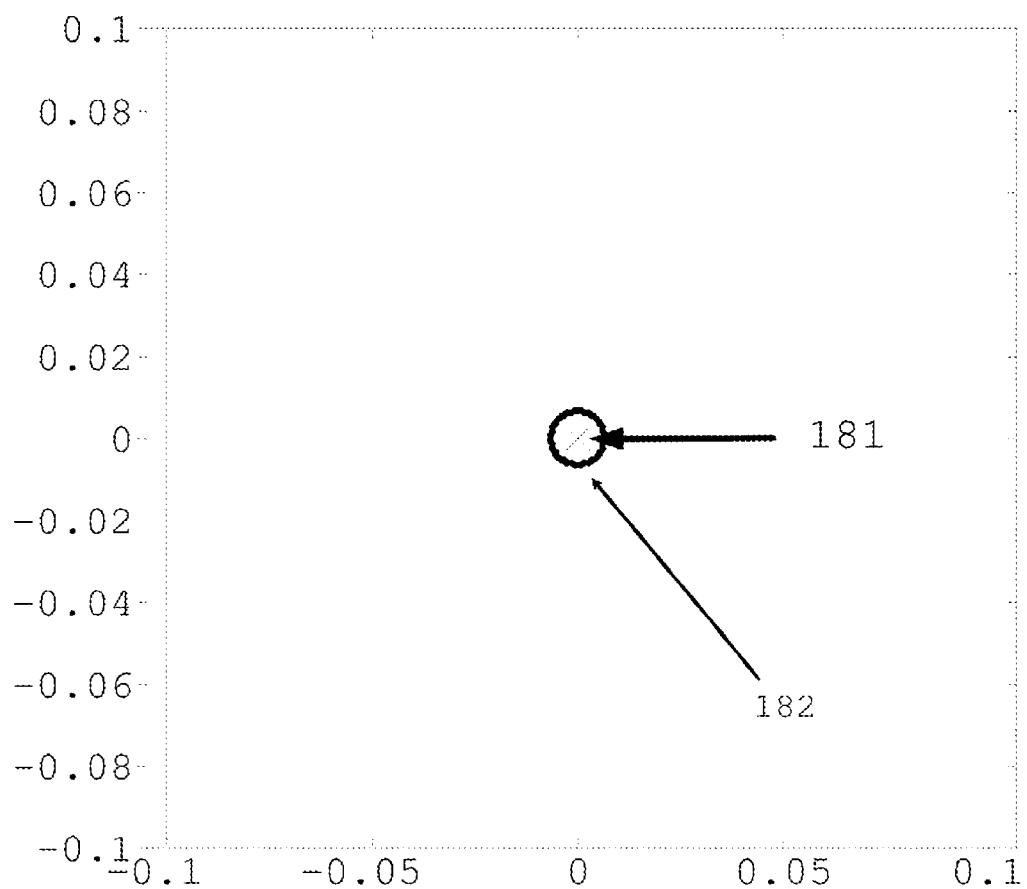
FIG. 10b shows an example of the size of the reconstructable region in accordance with prior art.

FIG. 10a illustrates how the size of the reconstructable region (172) can be increased by using a moving axis of rotation (171). In this figure the trajectory of the axis of rotation (171) is a spiral, but other forms of curves or paths can be used. In accordance with the current invention the extra oral dental x-ray imaging system has a mode for performing partial CT or 3D of a region of interest whereby the axis of rotation moves which allows unlimited size of the reconstructable region assuming enough time is given to traverse the desired path. FIGS. 10a and 10b are in the same scale, and the x, y axis units are in meters.

Figure 11A:
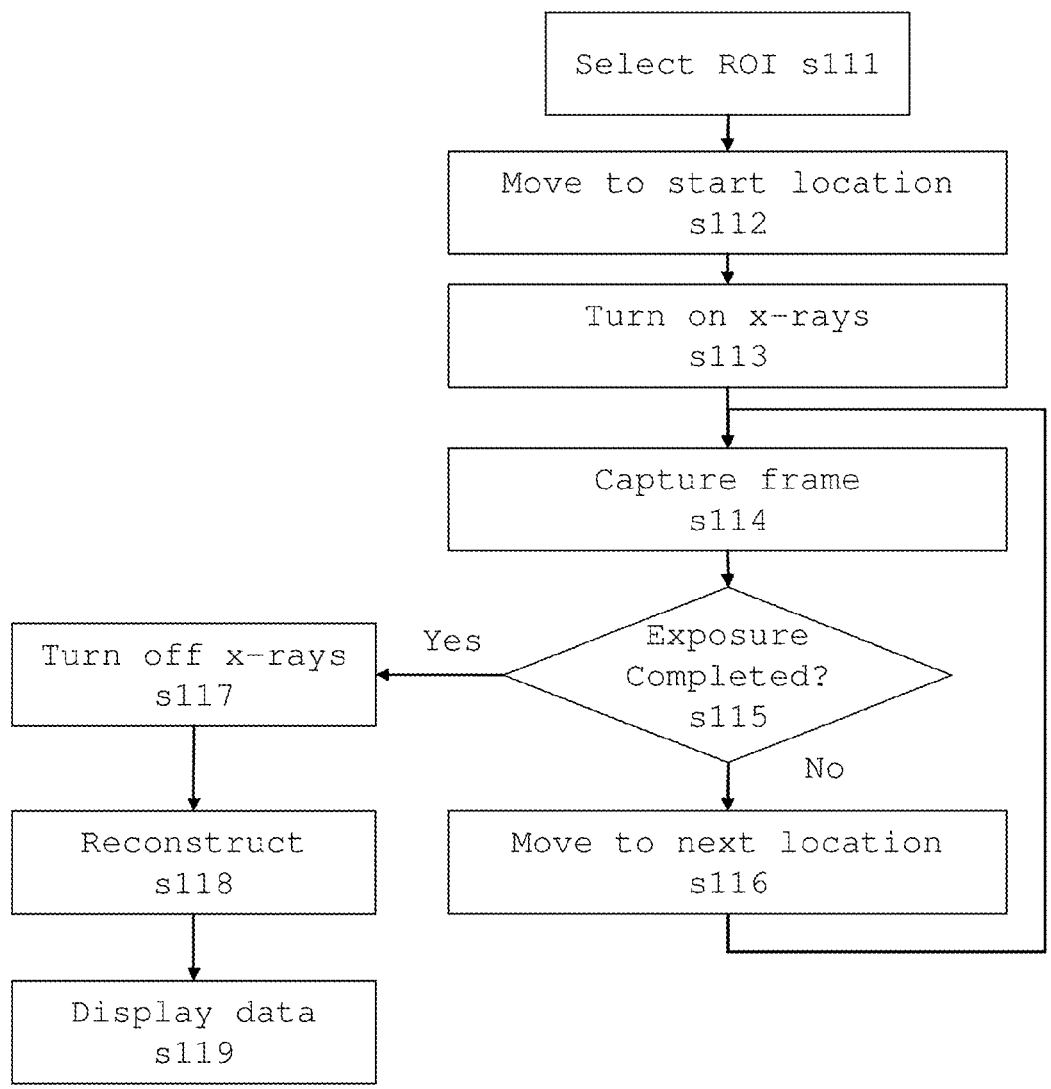
FIGS. 11a and 11b show a flow chart of an example algorithm used to reconstruct the region of interest in accordance with the current invention.
Figure 11B:
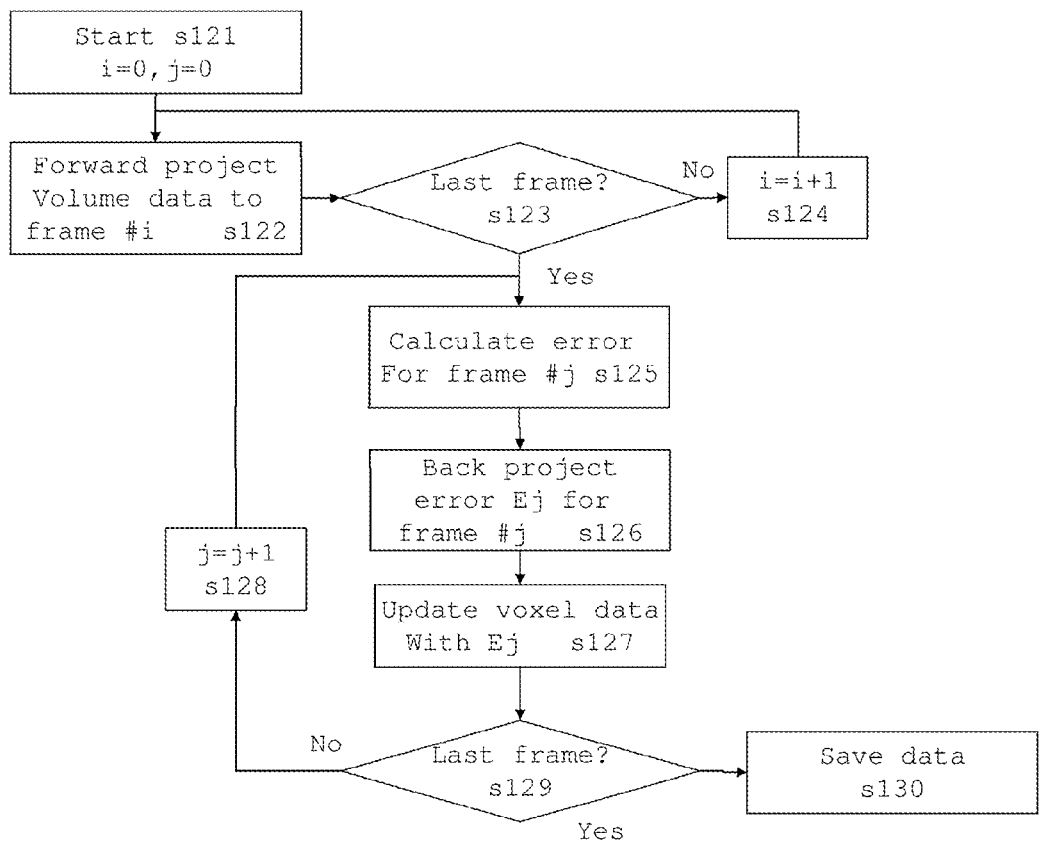

With reference now to FIGS. 11a and 11b we provide example algorithms which can be used to exemplify how the data can be collected and how an CT or 3D image can be reconstructed in a system in accordance with the current invention.

FIG. 11a shows a flowchart of data collection in accordance with the current invention. A region of interest is chosen by the user (s111). After that the system moves to the initial position (the start of the path for the axis of rotation) (s112). Next the x-rays are turned on (s113) and frames are captured (s114) until the exposure is completed (s115). The manipulator on the unit moves the x-ray source, imaging device and the axis of rotation between captures frames (s116). In practice the movement is continuous with continuous x-rays flux, but the system can also use a pulse type x-ray source and non-continuous movement. After all the frames are captures the x-rays are turned off (s117), data is reconstructed (s118) and the reconstructed image is displayed to the user (s119).

FIG. 11b shows the outline flowchart of the reconstruction algorithm which can be implemented using a CPU, GPU, FPGA or any other programmable device with suitable amount of memory. First the counter variables are initialized to point to the first frame (frame #0) (s121). Then the current estimate for the volume data is projected to frame the frame #i (s122). This repeated (s123) until all frames have been processed. The counter is increased (s124) to point to the next frame after the current frame has been processed.

After all the forward projections (i.e. projecting the 3D volume to 2D frames) have been calculated, the error between current simulated and collected data is calculated (s125). Then this error is backprojected to the volume elements, i.e. the contribution of each volume element to the error is calculated (s126). After the backprojection the volume estimate is updated based on some update formula, (s127), the simplest being to move each volume element to the direction of smaller error. A more sophisticated update rule like ART, Statistical inversion or conjugate gradient can also be used. The update can also be done on frame-by-frame basis of the update can process the frames in batches. The backprojection loop is run until all the frames have been processed (s129), a counter variable being incremented (s128) in the loop back. The frame counter is positioned to next frame between iterations (s130).

The algorithm in FIG. 11b is repeated until the volume estimate is accepted.

The distinct and breakthrough advantage of the aforementioned invention is that a digital sensor of limited active area can be utilized as part of the above system to allow partial CT or partial 3D reconstruction of useful sizes. For example with a sensor of active area of 25 mm (Width)×75 mm(Height)+6 mm×75 mm and two rotations in a spiral or approximate spiral with a total movement of the axis by 25 mm (see FIG. 10a), we can reconstruct a region of interest of 50 mm as can be seen in FIG. 10a. With three rotations and movement of the axis by approximately 35 mm we can reconstruct a region of interest of 80 mm (for clarification FIG. 10a shows only the two rotations example). Therefore while in a conventional dental CT system a 25 mm wide detector would only produce 25 mm/2 (magnification)=12.5 mm reconstructed volume, in the system in accordance with the current invention the reconstructed volume is four (4) times larger with two rotations in an approximate spiral trajectory and is six (6) times larger if three rotations are used. Obviously as one uses more and more rotations to make a larger spiral, the reconstructed volume increase to the limit that one can with a small detector active area reconstruct the entire object of interest, for example the entire anterior and posterior. Additionally it should be noted that the usefulness of this invention can be materialized even for small movements of the axis of rotation during the exposure profile. For example even one or more millimeters of movement of the axis of rotation will be beneficial. The implication of this invention is that high end extra-oral dental x-ray imaging systems utilize a single sensor with panoramic exposure mode and partial CT/3D exposure mode providing outstanding image quality, enough size of reconstructed CT/3D volume at affordable prices. Such systems serve the orthodontists who care about high quality panoramic images as well as implantologists and surgeons who need high quality CT and 3D images. Preferably the detector is a CdTe-CMOS or CdZnTe-CMOS detector which has distinct advantages in terms of readout speed, sensitivity and sharp image formation due to the fact that x-rays are converted directly to electronic signal. Other detector technologies can be used such as scintillators coupled to CCDs or CMOSes, flat panels etc.

Figure 12A:
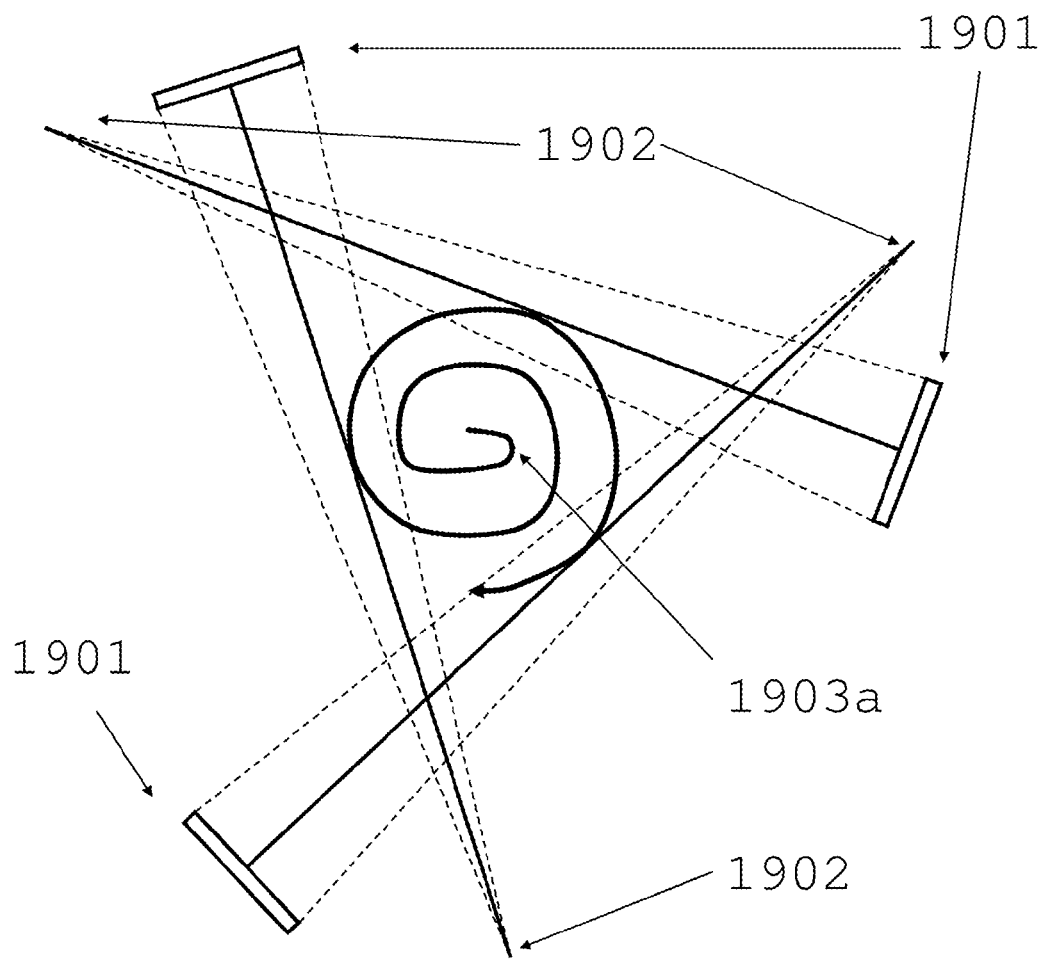
FIGS. 12a, 12b, 12c, 12d show alternative trajectories along which the axis of rotation can move in an exposure profile to perform partial CT or partial 3D of a region of interest with a system in accordance with the current invention.

In accordance with another aspect of the current invention the extra oral dental x-ray imaging system is configured to perform a CT or partial CT exposure characterized in that the line that connects the x-ray source focal spot and the middle part of the detector is tangential or approximately tangential to the trajectory of the axis of rotation during the exposure, or within a range of ±45 degrees from the tangential to the trajectory. This is illustrated in FIG. 12a, where the line connecting the mid-point of the imaging device (1901) to the focal spot of the x-ray source (1902) is tangential at that part to the trajectory along which the axis of rotation is moving. But as mentioned there can be also a deviation from the tangential in the range of ±45 degrees. This exposure profile allows the size of the region to be reconstructed to expand as the axis of rotation moves along the spiral. (1903a) The position of the x-ray source and the detector can be exchanged without departing from the scope of the invention.

Figure 12B:
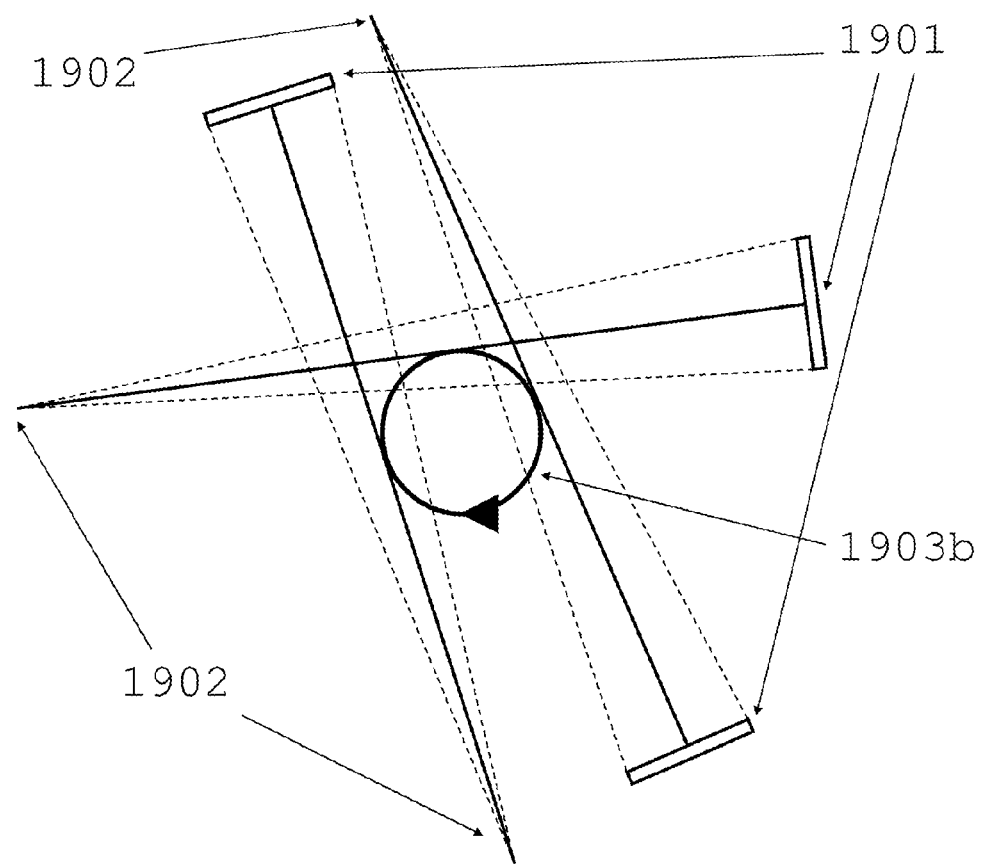
Figure 12C:
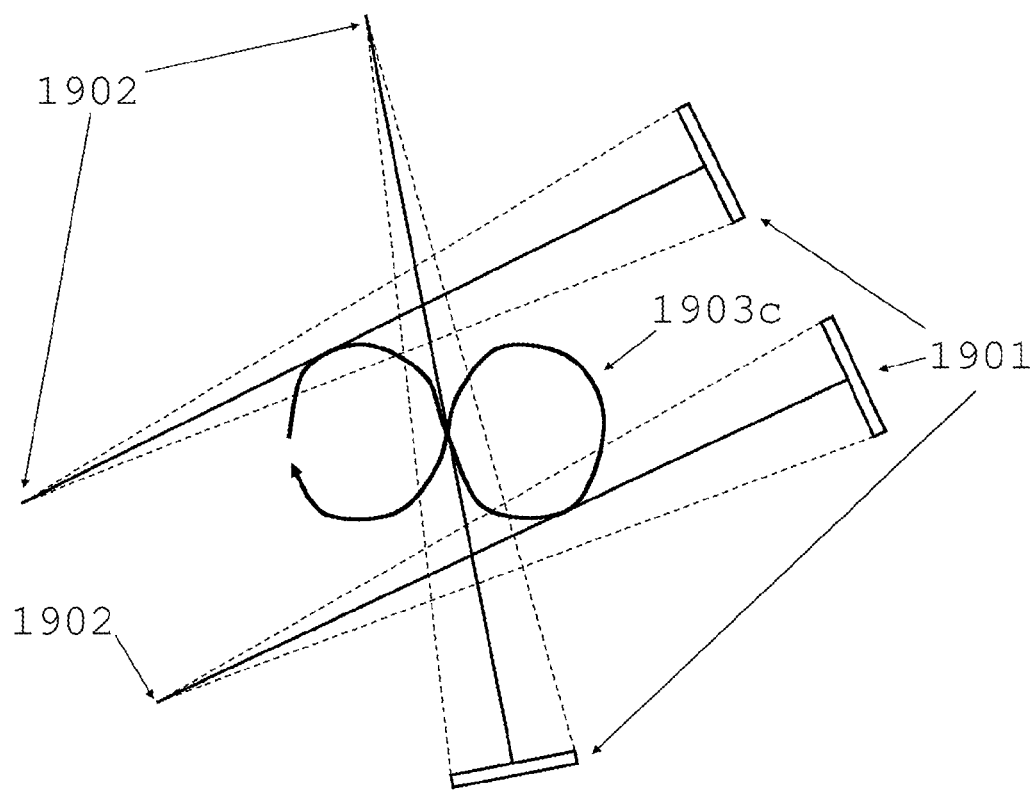
Figure 12D:
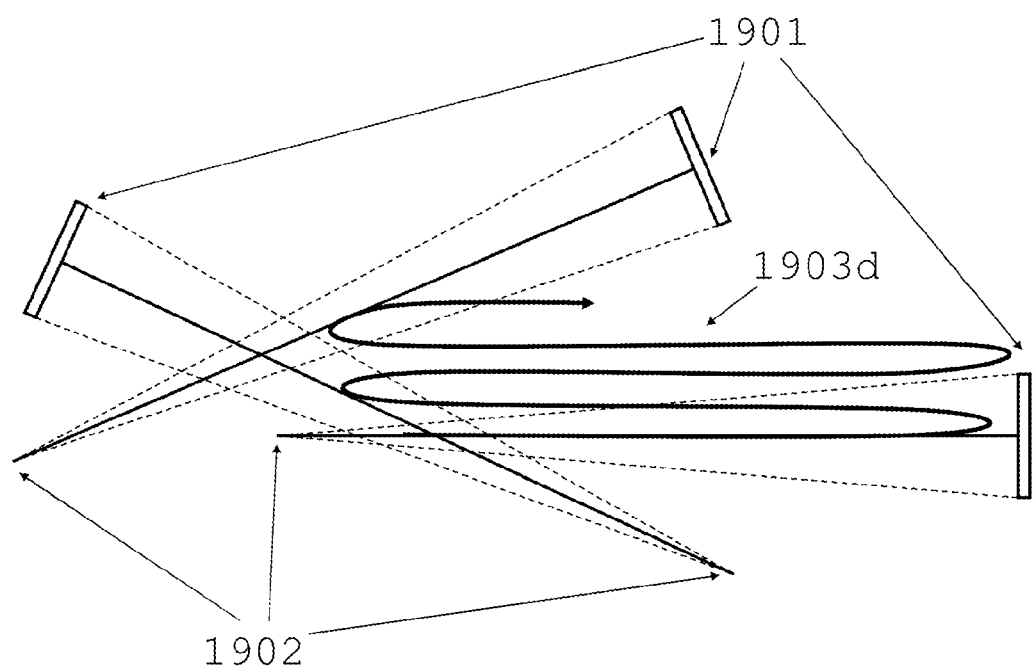

While preferred embodiments have been given and described with respect to the aforementioned figures, the scope of the invention covers any situation where the axis of rotation is moving during the partial CT exposure or CT exposure. The trajectory of the axis of rotation may indeed be an approximate spiral or deformed spiral, or as is exemplified in FIGS. 12b, 12c and 12d, it can comprise part of a circle, (1903b ), a circle or multiple circles depending how large volume one wants to reconstruct (FIG. 12b), it can be an "S" shaped trajectory (1903d,) (FIG. 12d), an "8" shaped trajectory (1903c, (FIG. 12c).

Figure 12E:
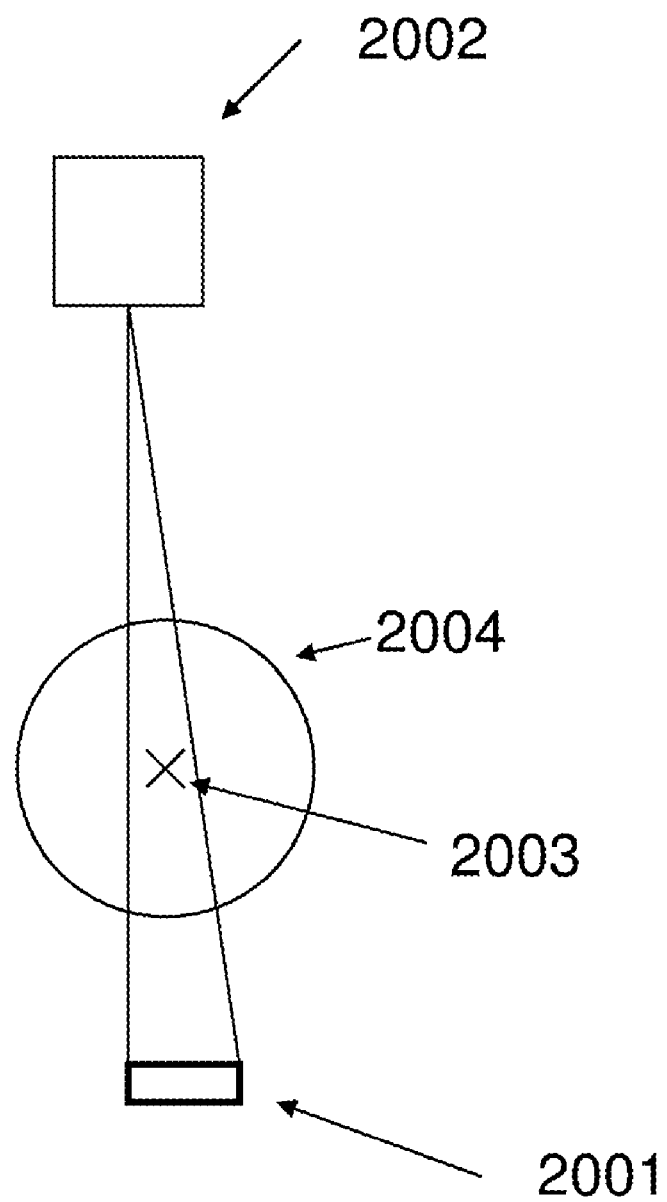
FIGS. 12e-f illustrate an effect of moving axis of rotation can also be achieved without physically moving the axis of rotation.
Figure 12F:
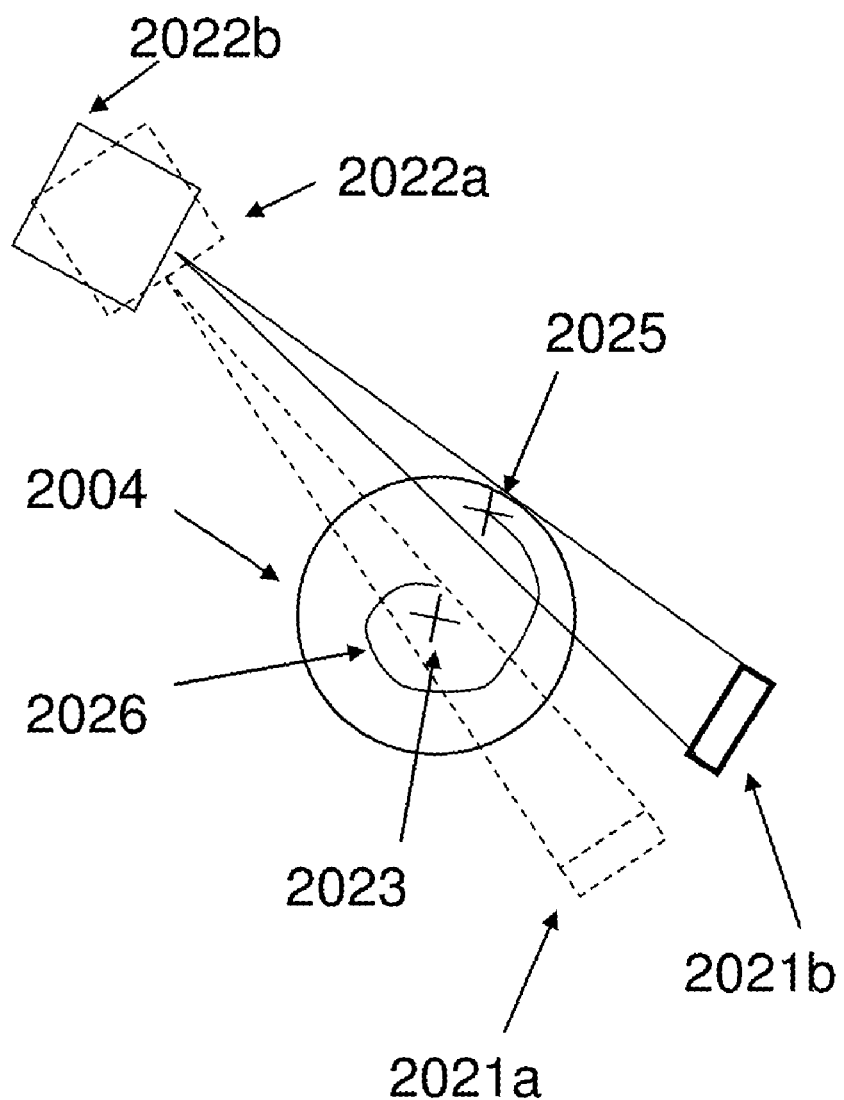

The effect of moving axis of rotation can also be achieved without physically moving the axis of rotation, but instead providing additional manipulator(s) for moving the imaging device and/or the x-ray source relative to the system's rotational axis/axes. This is illustrated in FIGS. 12e and 12f. FIG. 12e illustrates the normal system with the imaging device (2001), x-ray source (2002), (fixed or moving) axis of rotation (2003) and the object to be images (2004). The geometry imaging device and the x-ray source are fixed with respect to the rotational axis. The rotational axis can be fixed or moving, but the figure illustrates the case of a fixed rotational axis for simplicity.

FIG. 12f illustrates this aspect of the invention. The geometry of the imaging device and the x-ray source is changed with respect to the rotational axis during the exposure. Also the relative geometry of the imaging device and the x-ray source can change to further increase the field of view. The only limitation being that the x-ray beam emitted by the x-ray source must be captured by the imaging device.

There are two points in the exposure illustrated in FIG. 12f. The first point includes the imaging device (2021a), the x-ray source (2022a), the axis of rotation (2023) and the object to be imaged (2004). The second point in the exposure (or in time) has different relative geometry. The relative geometry of the imaging device (2021b) and the x-ray source (2022b) has changed with respect to the axis of rotation (2023).

This change in the relative geometry creates a virtual rotational axis (2025) which moves along a curve (2026) which in the case of FIG. 12f is a spiral even though any other curve mentioned earlier is suitable. The end effect of this is that the rotational axis can be fixed while still obtaining similar results for expanding the field of view as in others aspects of the invention.

Figure 12G:
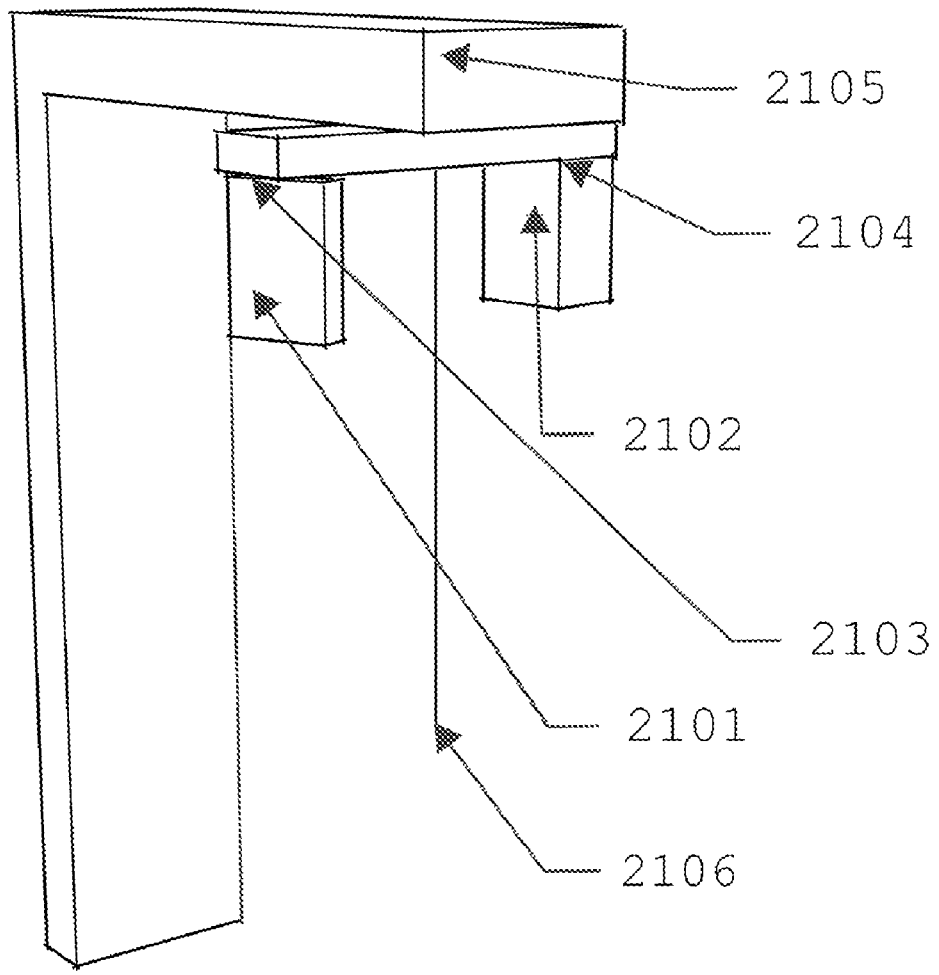
FIG. 12g illustrates an extra-oral dental x-ray imaging system relating to the embodiment of FIGS. 12e-f.

In accordance therefore with this aspect of the current invention we provide as illustrated in FIG. 12g an extra-oral dental x-ray imaging system, for performing a partial CT or partial 3D image of a region of interest of an object comprising:
- a) an x-ray source (2102) for exposing an object to x-rays so that the object may be imaged during the exposure;
- b) a x-ray imaging device (2101) suitable for producing multiple radiated image frames during at least part of the exposure;
- c) a manipulator (2105) for moving the imaging device and the x-ray source along a path between plural positions corresponding to plural radiated image frames during the exposure, the manipulator enabling movement of the x-ray source and the imaging device by selective translation and selective rotation about at least one rotational axis (2106) located between a focal point of the x-ray source and the x-ray imaging device; and either of both of the following
- d) additional manipulator (2103) for translating or rotating the imaging device during at least part of the exposure with respect to the rotational axis of the system
- e) additional manipulator (2104) for translating or rotating the x-ray source during at least part of the exposure with with respect to the rotational axis of the system The movement of the imaging device and the x-ray source shall be synchronized so that the x-ray beam originating from the x-ray source is captured by the imaging device.

The manipulator for moving the x-ray source can include translation and rotation of the x-ray source, translation and rotation of the collimator or translation and rotation of any component causing the x-ray beam to be translated.

What we claim is:

1. An extra-oral dental x-ray imaging system, for performing a partial CT or partial 3D image of a region of interest of an object, the system comprising:
   a) an x-ray source for exposing an object to x-rays so that the object may be imaged during the exposure;
   b) an x-ray imaging device suitable for producing multiple radiated image frames during at least part of the exposure;
   c) a first manipulator unit for moving the imaging device and the x-ray source along a path between plural positions corresponding to plural radiated image frames during the exposure, the manipulator unit configured for enabling movement of both the x-ray source and the imaging device by selective rotation about at least one rotational axis located between a focal point of the x-ray source and the x-ray imaging device, wherein during the exposure the manipulator unit moves the imaging device and the x-ray source about the at least one rotational axis;
   d) a second manipulator unit configured for providing at least one of translation and rotation of the x-ray source; and
   e) a third manipulator unit configured for providing at least one of translating and rotating the imaging device,
   said second and third manipulators being separate from each other and separate from said first manipulator unit and configured for translation and rotation the imaging device and x-ray source independently of each other and independently of the first manipulator, and relative to the axis of rotation during at least part of the exposure so that during the exposure the rotational axis is virtually moved along a curve due to the at least one of translation and rotation of the x-ray source and of the imaging device respectively provided by the first and second manipulators.

2. An extra-oral dental x-ray imaging system according to claim 1, wherein,
   during the at least part of the exposure the rotational axis is virtually moved along the curve without physically moving the axis of rotation, by
   i) the first manipulator unit rotating the imaging device and the x-ray source along the path during the at least part of the exposure about the one rotational axis without the one rotational axis moving,
   ii) the second manipulator unit translating or rotating the x-ray source during the exposure,
   iii) third manipulator unit translating or rotating the at least part of the imaging device during the exposure, and
   the curve defines a spiral.

3. An extra-oral dental x-ray imaging system according to claim 1, wherein through i) the first manipulator unit moving the imaging device and the x-ray source along a path between plural positions corresponding to plural radiated image frames during the exposure, the first manipulator unit moving both the x-ray source and the imaging device by both selective translation and selective rotation about the at least one rotational axis located between the focal point of the x-ray source and the x-ray imaging device, and ii) the third manipulator unit rotating the imaging device during at least part of the exposure with respect to the rotational axis, during the exposure the geometry of the imaging device and the x-ray source is changed with respect to the rotational axis.

4. An extra-oral dental x-ray imaging system according to claim 1, wherein through i) the first manipulator unit moving the imaging device and the x-ray source along a path between plural positions corresponding to plural radiated image frames during the exposure, the first manipulator unit moving both the x-ray source and the imaging device by both selective translation and selective rotation about the at least one rotational axis located between the focal point of the x-ray source and the x-ray imaging device, and ii) the second manipulator unit rotating the x-ray source during at least part of the exposure with respect to the rotational axis, during the exposure the geometry of the imaging device and the x-ray source is changed with respect to the rotational axis.

5. An extra-oral dental x-ray imaging system according to claim 1, wherein through i) the first manipulator unit moving the imaging device and the x-ray source along a path between plural positions corresponding to plural radiated image frames during the exposure, the first manipulator unit moving both the x-ray source and the imaging device by both selective translation and selective rotation about the at least one rotational axis located between the focal point of the x-ray source and the x-ray imaging device, and ii) the third manipulator unit translating the imaging device during at least part of the exposure with respect to the rotational axis, during the exposure the relative geometry of the imaging device and the x-ray source changes to further increase the field of view.

6. An extra-oral dental x-ray imaging system according to claim 1, wherein through i) the first manipulator unit moving the imaging device and the x-ray source along a path between plural positions corresponding to plural radiated image frames during the exposure, the first manipulator unit moving both the x-ray source and the imaging device by both selective translation and selective rotation about the at least one rotational axis located between the focal point of the x-ray source and the x-ray imaging device, and ii) the second manipulator unit translating the x-ray source during at least part of the exposure with respect to the rotational axis, during the exposure the relative geometry of the imaging device and the x-ray source changes to further increase the field of view.

7. An extra-oral dental x-ray imaging system according to claim 1, wherein through i) the first manipulator unit moving the imaging device and the x-ray source along a path between plural positions corresponding to plural radiated image frames during the exposure, the first manipulator unit moving both the x-ray source and the imaging device by both selective translation and selective rotation about the at least one rotational axis located between the focal point of the x-ray source and the x-ray imaging device, and ii) the third manipulator unit translating and rotating the imaging device during at least part of the exposure with respect to the rotational axis, during the exposure the rotational axis is virtually moved along a spiral.

8. An extra-oral dental x-ray imaging system according to claim 1, wherein through i) the first manipulator unit moving the imaging device and the x-ray source along a path between plural positions corresponding to plural radiated image frames during the exposure, the first manipulator unit moving both the x-ray source and the imaging device by both selective translation and selective rotation about the at least one rotational axis located between the focal point of the x-ray source and the x-ray imaging device, and ii) the second manipulator unit translating and rotating the x-ray source during at least part of the exposure with respect to the rotational axis, the rotational axis is virtually moved along the curve by defining a spiral.

9. An extra-oral dental x-ray imaging system according to claim 1, wherein through the third manipulator unit translating and rotating the imaging device during at least part of the exposure with respect to the rotational axis, during the exposure the rotational axis is virtually moved, without physically moving the axis of rotation, along the curve by defining a spiral.

10. An extra-oral dental x-ray imaging system according to claim 1, wherein through the second manipulator translating and rotating the x-ray source during at least part of the exposure with respect to the rotational axis, the rotational axis is virtually moved, without physically moving the axis of rotation, along a spiral.

11. An extra-oral dental x-ray imaging system according to claim 1, wherein through the second and third manipulator units translating and rotating respectively the x-ray source and imaging device during at least part of the exposure with respect to the rotational axis, the rotational axis is virtually moved without physically moving the axis of rotation.

12. An extra-oral dental x-ray imaging system, for performing a partial CT or partial 3D image of a region of interest of an object, the system comprising:
   a) an x-ray source for providing an x-ray beam for exposing an object to x-rays so that the object may be imaged during the exposure;
   b) an x-ray imaging device suitable for producing multiple radiated image frames during at least part of the exposure;
   c) a manipulator unit for moving the imaging device and the x-ray source along a path between plural positions corresponding to plural radiated image frames during the exposure, the manipulator unit configured for enabling movement of both the x-ray source and the imaging device by selective translation and selective rotation about a rotational axis located between a focal point of the x-ray source and the x-ray imaging device, wherein during the exposure the manipulator unit moves the imaging device and the x-ray source in at least one of translation and rotation about the at least one rotational axis, the manipulator unit comprising i) a first manipulator configured for selective translation of both the x-ray source and the imaging device, ii) a second manipulator configured for selective rotational movement of both the x-ray source and the imaging device; and
   d) an additional manipulator, separate from said first and second manipulators, configured for translating or rotating at least one of i) the imaging device during at least part of the exposure with respect to the rotational axis, and ii) a component causing effectively the x-ray source to be translated or rotated during at least part of the exposure with respect to the rotational axis so that during the exposure the rotational axis is virtually moved, without physically moving the axis of rotation, along a curve.

13. An extra-oral dental x-ray imaging system according to claim 12, wherein the component is the x-ray source and the curve is a spiral.

14. An extra-oral dental x-ray imaging system according to claim 13, wherein through i) the manipulator unit moving the imaging device and the x-ray source along a path between plural positions corresponding to plural radiated image frames during the exposure, the manipulator unit moving both the x-ray source and the imaging device by selective rotation about the at least one rotational axis located between the focal point of the x-ray source and the x-ray imaging device, and ii) the additional manipulator translating the x-ray source during at least part of the exposure with respect to the rotational axis, during the exposure the geometry of the imaging device and the x-ray source is changed with respect to the rotational axis and the curve is a spiral.

15. An extra-oral dental x-ray imaging system according to claim 13, wherein through i) the manipulator unit moving the imaging device and the x-ray source along a path between plural positions corresponding to plural radiated image frames during the exposure, the manipulator unit moving both the x-ray source and the imaging device by at least one of selective translation and selective rotation about the at least one rotational axis located between the focal point of the x-ray source and the x-ray imaging device, and ii) the additional manipulator rotating the x-ray source during at least part of the exposure with respect to the rotational axis, during the exposure the relative geometry of the imaging device and the x-ray source changes to further increase the field of view and the curve is a spiral.

16. An extra-oral dental x-ray imaging system according to claim 13, wherein through i) the manipulator unit moving the imaging device and the x-ray source along a path between plural positions corresponding to plural radiated image frames during the exposure, the manipulator unit moving both the x-ray source and the imaging device by at least one of selective translation and selective rotation about the at least one rotational axis located between the focal point of the x-ray source and the x-ray imaging device, and ii) the additional manipulator translating and rotating the x-ray source during at least part of the exposure with respect to the rotational axis, the rotational axis is virtually moved, without physically moving the axis of rotation, along a spiral.

17. An extra-oral dental x-ray imaging system according to claim 12, wherein through i) the manipulator unit moving the imaging device and the x-ray source along a path between plural positions corresponding to plural radiated image frames during the exposure, the manipulator unit moving both the x-ray source and the imaging device by at least one of selective translation and selective rotation about the at least one rotational axis located between the focal point of the x-ray source and the x-ray imaging device, and ii) the additional manipulator rotating the imaging device during at least part of the exposure with respect to the rotational axis, during the exposure during the exposure the geometry of the imaging device and the x-ray source is changed with respect to the rotational axis and the curve is a spiral.

18. An extra-oral dental x-ray imaging system according to claim 12, wherein through i) the manipulator unit moving the imaging device and the x-ray source along a path between plural positions corresponding to plural radiated image frames during the exposure, the manipulator unit moving both the x-ray source and the imaging device by at least one of selective translation and selective rotation about the at least one rotational axis located between the focal point of the x-ray source and the x-ray imaging device, and ii) the additional manipulator translating the imaging device during at least part of the exposure with respect to the rotational axis, during the exposure the rotational axis is moved, without physically moving the axis of rotation, along a spiral.

19. An extra-oral dental x-ray imaging system according to claim 13, wherein through i) the manipulator unit moving the imaging device and the x-ray source along a path between plural positions corresponding to plural radiated image frames during the exposure, and ii) the additional manipulator translating and rotating the the imaging device during at least part of the exposure with respect to the rotational axis, during the exposure the rotational axis is virtually moved, without physically moving the axis of rotation and the curve is a spiral.

20. An extra-oral dental x-ray imaging system, for performing a partial CT or partial 3D image of a region of interest of an object, the system comprising:
   a) an x-ray source for exposing an object to x-rays so that the object may be imaged during the exposure;
   b) an x-ray imaging device suitable for producing multiple radiated image frames during at least part of the exposure;
   c) a manipulator unit for moving the imaging device and the x-ray source along a path between plural positions corresponding to plural radiated image frames during the exposure, the manipulator unit configured for enabling movement of both the x-ray source and the imaging device by selective rotation about one rotational axis located between a focal point of the x-ray source and the x-ray imaging device, wherein during the exposure the manipulator unit moves the imaging device and the x-ray source about the one rotational axis with the one rotational axis remaining physical fixed; and
   d) an additional manipulator unit configured for providing translation of the x-ray source and the imaging device, the additional manipulator unit being separate from the manipulator unit, the additional manipulator unit configured to translate the x-ray source and the imaging device relative to the one rotational axis during at least part of the exposure so that during the exposure the rotational axis is virtually moved along a curve without physically moving the one axis of rotation.

21. An extra-oral dental x-ray imaging system according to claim 20, wherein,
   the additional manipulator unit comprises:
   i) a first additional manipulator for translating the imaging device along one direction, during the at least part of the exposure with respect to the one rotational axis of rotation, and
   ii) a second additional manipulator for translating the x-ray source along a second direction that is different from the first direction, during the at least part of the exposure with with respect to the rotational axis of rotation, and
   the curve defines a spiral.

* * * * *